US009758585B2

(12) United States Patent
Vairo et al.

(10) Patent No.: US 9,758,585 B2
(45) Date of Patent: *Sep. 12, 2017

(54) COMPOSITIONS AND METHODS FOR TARGETING TYPE 1 INTERFERON PRODUCING CELLS

(71) Applicant: CSL Limited, Parkville (AU)

(72) Inventors: Gino Luigi Vairo, Northcote (AU); Andrew Nash, Kew (AU); Eugene Maraskovsky, Kew (AU); Nick Wilson, Brighton East (AU); Samantha Busfield, Brunswick (AU); Con Panousis, Bundoora (AU)

(73) Assignee: CSL Limited, Parkville (AU)

( * ) Notice: Subject to any disclaimer, the term of this patent is extended or adjusted under 35 U.S.C. 154(b) by 0 days.

This patent is subject to a terminal disclaimer.

(21) Appl. No.: 14/617,882

(22) Filed: Feb. 9, 2015

(65) Prior Publication Data

US 2015/0147322 A1 May 28, 2015

Related U.S. Application Data

(63) Continuation of application No. 13/967,244, filed on Aug. 14, 2013, now abandoned, which is a continuation of application No. 13/579,886, filed as application No. PCT/AU2011/000155 on Feb. 17, 2011, now Pat. No. 8,535,669, and a continuation of application No. 12/707,297, filed on Feb. 17, 2010, now abandoned.

(60) Provisional application No. 61/374,489, filed on Aug. 17, 2010, provisional application No. 61/374,497, filed on Aug. 17, 2010, provisional application No. 61/153,470, filed on Feb. 18, 2009.

(51) Int. Cl.
| | |
|---|---|
| *C07K 16/24* | (2006.01) |
| *A61K 39/395* | (2006.01) |
| *C07K 16/28* | (2006.01) |
| *A61K 38/17* | (2006.01) |
| *A61K 38/20* | (2006.01) |
| *A61K 51/10* | (2006.01) |
| *C07K 16/18* | (2006.01) |
| *A61K 39/00* | (2006.01) |

(52) U.S. Cl.
CPC ...... *C07K 16/2866* (2013.01); *A61K 38/1793* (2013.01); *A61K 38/202* (2013.01); *A61K 39/3955* (2013.01); *A61K 51/1021* (2013.01); *A61K 51/1033* (2013.01); *C07K 16/244* (2013.01); *A61K 2039/505* (2013.01); *C07K 2317/21* (2013.01); *C07K 2317/24* (2013.01); *C07K 2317/41* (2013.01); *C07K 2317/52* (2013.01); *C07K 2317/72* (2013.01); *C07K 2317/73* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,143,871 A | 11/2000 | Bonnefoy et al. | |
| 6,159,443 A | 12/2000 | Hallahan | |
| 6,177,078 B1 | 1/2001 | Lopez | |
| 6,733,743 B2 | 5/2004 | Jordan | |
| 8,163,279 B2 | 4/2012 | Bergstein | |
| 8,535,669 B2 | 9/2013 | Vairo et al. | |
| 2007/0071675 A1 | 3/2007 | Wu et al. | |
| 2007/0135620 A1 | 6/2007 | Chamberlain et al. | |
| 2008/0260731 A1 | 10/2008 | Bernett et al. | |
| 2010/0209341 A1 | 8/2010 | Vairo et al. | |
| 2013/0084282 A1 | 4/2013 | Vairo et al. | |
| 2013/0137855 A1 | 5/2013 | Panousis | |
| 2014/0178364 A1 | 6/2014 | Vairo et al. | |
| 2015/0017180 A1 | 1/2015 | Vairo et al. | |

FOREIGN PATENT DOCUMENTS

| | | |
|---|---|---|
| EP | 0489116 | 4/1994 |
| WO | WO 94/12638 | 6/1994 |
| WO | WO 95/00646 | 1/1995 |
| WO | WO 97/24373 | 7/1997 |
| WO | WO 97/28190 | 8/1997 |
| WO | WO 00/09561 | 2/2000 |
| WO | WO 00/47620 | 8/2000 |
| WO | WO 00/66632 | 11/2000 |
| WO | WO 02/090510 | 11/2002 |
| WO | WO 03/087815 | 10/2003 |
| WO | WO 2005/069933 | 8/2005 |
| WO | WO 2008/024188 | 2/2008 |
| WO | WO 2008/122735 | 10/2008 |
| WO | WO 2009/070844 | 6/2009 |

(Continued)

OTHER PUBLICATIONS

Brummell et al. Biochemistry; 1993, vol. 32, pp. 1180-1187.*
MacCallum et al. J Mol Biol., 1996, vol. 262, pp. 732-745.*
De Pascalis et al. The Journal of Immunology; 2002; vol. 169, pp. 3076-3084.*
Casset et al. Biochemical and Biophysical Research Communications; 2003; vol. 307, pp. 198-205.*
Chen et al. J Mol Biol, 1999; vol. 293, pp. 865-881.*
Sun et al, Blood, 1996; vol. 87, No. 1. pp. 83-92.*
Blanco et al, Science, 2001, vol. 294, pp. 1540-1543.*
Miyashita et al, Acta Derm Venereol. 2014; vol. 94, No. 5, pp. 563-567.*
Wu et al. (J Mol Biol. 1999, vol. 294; pp. 151-162.*

(Continued)

*Primary Examiner* — Bridget E Bunner
*Assistant Examiner* — Fozia Hamud
(74) *Attorney, Agent, or Firm* — Cooley LLP

(57) ABSTRACT

The present disclosure provides a method for treating lupus, Sjörgen's syndrome or scleroderma, the method comprising administering to the mammal an immunoglobulin which binds an interleukin 3 receptor α (IL-3Rα) chain and which depletes or at least partly eliminates plasmacytoid dendritic cells (p DCs) and basophils to which it binds.

16 Claims, 6 Drawing Sheets

(56) References Cited

FOREIGN PATENT DOCUMENTS

| WO | WO 2010/094068 | 8/2010 |
|----|----------------|--------|
| WO | WO 2010/126066 | 11/2010 |
| WO | WO 2011/100786 | 8/2011 |
| WO | WO 2012/021934 | 2/2012 |

OTHER PUBLICATIONS

Tomasini et al, Journal of Cutaneous Pathology, 2010, vol. 37, pp. 1132-1139.*
Crow et al, Rheum Dis Clin North Am. Feb. 2010; 36(1); pp. 1-13.*
Rowland et al, The Journal of Experimental Medicine, 2014, vol. 211, No. 10, pp. 1977-1990.*
Brorson et al., "Mutational analysis of avidity and fine specificity of anti-levan antibodies." The Journal of Immunology, 163(12): 6694-6701 (1999).
Bruhl, H. et al., "Important role of interleukin-3 in the early phase of collagen-induced arthritis," Arthritis & Rheumatism, 60(5):1352-1361 (2009).
Cheung, D. L. et al., "Regulation of human monocyte DNA synthesis by colony-stimulating factors, cytokines, and cyclic adenosine monophosphate," Blood, 79(8):1972-1981 (1992).
Colman, P.M., "Effects of amino acid sequence changes on antibody-antigen interactions." Research in Immunology, 145: 33-36 (1994).
Cook, A. D. et al., "Blockade of collagen-induced arthritis post-onset by antibody to granulocyte-macrophage colony-stimulating factor (GM-CSF): requirement for GM-CSF in the effector phase of disease," Arthritis Res., 3:293-298 (2001).
Dall'Era, M. C. et al., "Type I interferon correlates with serological and clinical manifestations of SLE," Annals of the Rheumatic Diseases, 64(12): 1692-1697 (2005).
Dorssers, L. C. J. et al., "Receptor and antibody interactions of human interleukin-3 characterized by mutational analysis," The Journal of Biological Chemistry, 266(31):21310-21317 (1991).
Ebner, S. et al., "A novel role for IL-3: human monocytes cultured in the presence of IL-3 and IL-4 differentiate into dendritic cells that produce less IL-12 and shift Th cell responses toward a Th2 cytokine pattern," The Journal of lmmunoloav., 168:6199-6207 (2002).
Examination Report for Australian Patent Application No. 2011217728, dated Sep. 21, 2012, 3 pages.
Examination Report for United Kingdom Application No. GB1211289.2, dated Oct. 31, 2012, 2 pages.
Farkas, L. et al., "Plasmacytoid dendritic cells (natural interferon-alpha/beta-producing cells) accumulate in cutaneous lupus erythematosus lesions," American Journal of Pathology, 159(1):237-243 (2001).
Feghali and Wright, "Cytokines in acute and chronic inflammation." Front Biosci, 2(1): d12-d26 (1997).
Ferraccioli, G. et al., "Circulating levels of interleukin 10 and other cytokines in rheumatoid arthritis treated with cyclosporin A or combination therapy," J Rheumatol., 25(10):1874-1879 (1998).
Ferrer, M. et al., "IL3 effect on basophils histamine release upon stimulation with chronic urticaria sera," Allergy, 58(8):802-807 (2003).
Ferrer, M. et al., "Progress and challenges in the understanding of chronic urticaria," Allergy, Asthma, and Clinical Immunology, 3(1):31-35 (2007).
Firestein, G. S. et al., "Cytokines in chronic inflammatory arthritis. I. Failure to detect T celllymphokines (interleukin 2 and interleukin 3) and presence of macrophage colony-stimulating factor (CSF-1) and a novel mast cell growth factor in rheumatoid synovitis," J Exp Med., 168:1573-1586 (1988).
Frezzolini, A. et al., "Serum-induced basophil CD63 expression by means of a tricolour flow cytometric method for the in vitro diagnosis of chronic urticaria," Allergy, 61 (9): 1071-1077 (2006).
Hart, P. H. et al., "Regulation by interleukin-3 of human monocyte pro-inflammatory mediators. Similarities with granulocyte-macrophage colony-stimulating factor," Immunology, 71(1):76-82 (1990).

Heller, R. A. et al., "Discovery and analysis of inflammatory disease-related genes using eDNA microarrays," Proc Natl Acad Sci USA, 94(6):2150-2155 (1997).
Hermes, B. et al., "Upregulation of TNF-alpha and IL-3 expression in lesional and uninvolved skin in different types of urticaria," Journal of Allergy and Clinical Immunology, 103(2):307-314 (1999).
International Search Report and Written Opinion for International Application No. PCT/AU2008/001797, mailed Feb. 23, 2009, 10 pages.
International Preliminary Report on Patentability for International Application No. PCT/AU2008/001797, mailed Jun. 8, 2010, 8 pages.
International Search Report and Written Opinion for International Application No. PCT/AU2010/000178, mailed Mar. 29, 2010, 9 pages.
International Preliminary Report on Patentability for International Application No. PCT/AU2010/000178, mailed Aug. 21, 2012, 5 pages.
International Search Report and Written Opinion for International Application No. PCT/AU2011/001056, mailed Nov. 1, 2011, 13 pages.
International Preliminary Report on Patentability for International Application No. PCT/AU2011/001056, mailed Feb. 19, 2013, 7 pages.
International Search Report and Written Opinion for PCT/AU2011/000155, mailed on Apr. 4, 2011, 12 pages.
International Preliminary Report on Patentability for PCT/AU2011/000155, mailed on Aug. 21, 2012, 8 pages.
Jin et al., "Monoclonal Antibody-Mediated Targeting of CD123, IL-3 Receptor a Chain, Eliminates Human Acute Myeloid Leukemic Stem Cells." Cell Stem Cell, 5: 31-42 (2009).
Kaplan, A. P. et al., "Treatment of chronic autoimmune urticaria with omalizumab," Journal of Allergy and Clinical Immunology, 122(3):569-573 (2008).
Kobayashi et al., "Tryptophan H33 plays an important role in pyrimidine (6-4) pyrimidone photoproduct binding by a high-affinity antibody." Protein Engineering, 12(10): 879-884 (1999).
Koike, K. et al., "Macrophage colony formation supported by purified CSF-1 and/or interleukin 3 in serum-free culture: evidence for hierarchical difference in macrophage colony-forming cells," Blood, 67(4):859-864 (1986).
Kopsidas, G. et al., "RNA mutagenesis yields highly diverse mRNA libraries for in vitro protein evolution," BMC Biotechnology, 7(1):18 (2007).
Lantz, C. S. et al., "Role for interleukin-3 in mast-cell and basophil development and in immunity to parasites," Nature, 392(6671):90-93 (1998).
Lazar et al., "Engineered antibody Fc variants with enhanced effector function." PNAS, 103(11): 4005-4010 (2006).
Lazar, G. A. et al, "Engineered antibody Fe variants with enhanced effector function," PNAS, 103(11 ): 4005-4010 (2006).
Lee, J. C. et al., "Effect of auranofin treatment on aberrant splenic interleukin production in adjuvant arthritic rats," The Journal of Immunology, 139(10):3268-3274 (1987).
Lippert, U. et al., "Inhibition of cytokine secretion from human leukemic mast cells and basophils by H1- and H2-receptor antagonists," Experimental Dermatology, 9(2):118-124 (2000).
Lourenco, F. D. et al., "Activated status of basophils in chronic urticaria leads to interleukin-3 hyperresponsiveness and enhancement of histamine release induced by anti-IgE stimulus," British Journal of Dermatology, 158(5):979-986 (2008).
McNiff, J. M. et al., "Plasmacytoid dendritic cells are present in cutaneous dermatomyositis lesions in a pattern distinct from lupus erythematosus," Journal of Cutaneous Pathology, 35(5):452-456 (2008).
Niewold, T. B., "Interferon alpha-induced lupus proof of principle," Journal of Clinical Rheumatology, 14(3):131-132 (2008).
Niewold, T.B., "Interferon alpha-induced lupus proof of principle." Journal of Clinical Rheumatology: Practical Reports on Rheumatic & Musculoskeletal Diseases, 14(3): 131-132 (2008).
Obata, K. et al., "Basophils are essential initiators of a novel type of chronic allergic inflammation," Blood, 110:913-920 (2007).

(56) References Cited

OTHER PUBLICATIONS

Office Action for Chinese Patent Application No. 2010800643171, dated Feb. 18, 2010, 2 pages.
Office Action for U.S. Appl. No. 13/256,926, mailed May 3, 2013, 13 pages.
Pascual et al., "Systemic lupus erythematosus: all roads lead to type I interferons." Current Opinion in Immunology (2006); 18: 1-7.
Roberts, A. W. et al., "A Phase 1 and correlative biological study of CSL360 (anti-CD123 mAb) in AML," Blood, 112(11):1015-1016 (2008).
Schroeder, J. T., "Human basophils secrete IL-3: Evidence of autocrine priming for phenotypic and functional responses in allergic disease," The Journal of Immunology, 182(4):2432-2438 (2009).
Stewart, T. A., "Neutralizing interferon alpha as a therapeutic approach to autoimmune diseases," Cytokine & Growth Factor Reviews, 14(2):139-154 (2003).
Stewart, T.A., "Neutralizing interferon alpha as a therapeutic approach to autoimmune diseases." Cytokine & Growth Factor Reviews, 14(2): 139-154 (2003).
Supplementary European Search Report and Opinion for European Patent Application No. 10743324, mailed Jun. 21, 2013, 9 pages.
Supplementary European Search Report and Opinion for European Patent Application No. 11744183, mailed Aug. 5, 2013, 9 pages.
Supplementary European Search Report and Opinion for European Patent Application No. 11817577, mailed Jul. 30, 2013, 9 pages.
Tan, P. et al., "'Superhumanized' antibodies: reduction of immunogenic potential by complementarity determining region grafting with human germline sequences: Application to an anti-CD28," The Journal of Immunology, 169(2):1119-1125 (2002).
U.S. Appl. No. 12/707,297, Office Action mailed May 22, 2012, 16 pages.
U.S. Appl. No. 12/707,297, Office Action mailed Dec. 6, 2012, 18 pages.
U.S. Appl. No. 12/707,297, Office Action mailed Feb. 12, 2014, 12 pages.
U.S. Appl. No. 13/579,886, Notice of Allowance mailed Aug. 12, 2013, 5 pages.
U.S. Appl. No. 13/967,244, Office Action mailed Aug. 8, 2014, 16 pages.
Urosevic, M. et al., "Disease-independent skin recruitment and activation of plasmacytoid predendritic cells oil owing imiquimod treatment," Journal of the National Cancer Institute, 97(15): 1143-1153 (2005).
Wu, H., "Simultaneous humanization and affinity optimization of monoclonal antibodies," Chapter 12 in: Methods in Molecular Biology, vol. 207: Recombinant Antibodies for Cancer Therapy: Methods and Protocols, Welschof, M. et al. (eds.), Humana Press, Inc., Totowa, NJ, pp. 197-212 (2003).
Yamada, M. et al., "Effect of cytokines on the proliferation/differentiation of stroma-initiating cells," Journal of Cellular Physiology, 184(3):351-355 (2000).
Yamada, R. et al., "Association between a single-nucleotide polymorphism in the promoter of the human interleukin-3 gene and rheumatoid arthritis in Japanese patients, and maximum-likelihood estimation of combinatorial effect that two genetic loci have on susceptibility to the disease," Am. J. Hum. Genet., 68:674-685 (2001).
Yogesha, S. D. et al., "IL-3 inhibits TNF-alpha-induced bone resorption and prevents inflammatory arthritis," The Journal of Immunology, 182(1):361-370 (2009).
Oon, Shereen, et al., "A cytotoxic Anti-IL-3Rα Antibody Targets Key Cells and Cytokines Implicated in Systemic Lupus Erythematosus," JCI Insight, 1(6), Published May 5, 2016, 15 pages.

* cited by examiner

COMPOSITIONS AND METHODS FOR TARGETING TYPE 1 INTERFERON PRODUCING CELLS

RELATED APPLICATION DATA

The present application is a continuation of U.S. patent application Ser. No. 13/967,244 entitled "Compositions and Methods for Targeting Type I Interferon Producing Cells," filed on Aug. 14, 2013 (Abandoned), which is a continuation of U.S. patent application Ser. No. 13/579,886 entitled "Methods of Treating Lupus By Administering Humanized Anti-Interleukin 3 Receptor Alpha Chain Antibodies," filed on Dec. 18, 2012, which issued as U.S. Pat. No. 8,535,669, which is a '371 application of International Patent Application No. PCT/AU2011/000155 filed on Feb. 17, 2011, which claims priority from U.S. Provisional Application No. 61/374,497 entitled "Compositions and Methods for Targeting type I Interferon-Producing Cells" filed on 17 Aug. 2010, from U.S. Provisional Application No. 61/374,489 entitled "Humanized Anti-Interleukin 3 Receptor Alpha Chain Antibodies" filed on 17 Aug. 2010, and is a continuation of U.S. patent application Ser. No. 12/707,297 entitled "Treatment of Chronic Inflammatory Conditions" filed on 17 Feb. 2010 (Abandoned), which claims priority from U.S. Provisional Application No. 61/153,470 entitled "Treatment of Chronic Inflammatory Conditions" filed on Feb. 18, 2009. The entire contents of these applications are hereby incorporated by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is CSLL_004_05US_ST25.txt. The text file is 20 KB, was created on Feb. 9, 2015, and is being submitted electronically via EFS-Web.

FIELD

The present disclosure relates to treatment of inflammatory diseases.

BACKGROUND

The interferon (IFN) family of cytokines comprises both type I and type II subgroups. The type I subgroup is composed of IFNα, IFNω, IFNκ, IFNκ, and IFNτ and the type II subgroup is represented by IFNγ. Type I IFNs have multiple immunomodulatory effects including stimulation of polyclonal T cell responses, isotype switching, expression of class I major histocompatibility complex (MHC) molecules and induction of dendritic cell (DC) differentiation. Type I IFNs stimulate both macrophages and natural killer (NK) cells to elicit an anti-viral response, and are also active against tumors. Type I IFNs also act as pyrogenic factors by altering the activity of thermosensitive neurons in the hypothalamus, thus causing fever. A feature of the type I IFN system is rapid induction and amplification of signaling pathways, ensuring that a vigorous antiviral immune response is mounted.

However, while such pathways are highly effective for rapid virus eradication, this amplification can be maladapted in immune responses directed against host tissue, leading to autoimmune disease. Examples include systemic lupus erythematosus (SLE), rheumatoid arthritis and glomerulonephritis.

SLE is a chronic autoimmune disease in which immune defects lead to autoantibody production and subsequent inflammation and/or tissue damage in multiple organs, including skin, kidneys, blood, brain and joints. Disease course can be chronically active, relapsing and remitting or long-remitting. SLE is characterized by increased levels of many cytokines, including type I IFNs, such as IFNα.

Evidence for the role of IFNα in SLE has been demonstrated in several in vitro studies showing that serum from patients with SLE induced DC maturation from monocytes from normal mammals. Thus, serum from SLE patients could induce normally quiescent monocytes to become antigen presenting cells capable of inducing an immune response. Furthermore, suppression of IFNAR1 (the α chain of the receptor for type I IFN) expression in a mouse model of SLE (NZB mice) reduced hemolytic anemia, and reduced glomerulonephritis.

Clinically, patients with active SLE often have raised serum type I IFN levels, and these levels correlate positively with disease activity. Additional clinical evidence for a putative role of IFNα in SLE comes from the observation that patients without SLE treated with IFNα occasionally develop autoantibodies and clinical manifestations consistent with SLE.

Type I interferons are produced by many cell types including lymphocytes (NK cells, B-cells and T-cells), macrophages, fibroblasts, endothelial cells, osteoblasts and certain dendritic cells. Plasmacytoid dendritic cells (pDCs) have been identified as being the most potent producers of type I IFNs in response to foreign antigens. pDCs are a subtype of circulating dendritic cells found in the blood as well as in peripheral lymphoid organs that are a source of type I interferons. Human pDCs typically express the surface markers IL-3 receptor α chain (IL-3Rα, CD123), BDCA-2 (CD303) and BDCA-4 (CD304), but do not express CD11c or CD14, which distinguishes them from conventional dendritic cells or monocytes, respectively. Upon stimulation and subsequent activation, pDCs produce large amounts of type I interferons (mainly IFN-α and IFN-β).

Given the apparent role for IFNα in type I IFN-dependent inflammatory diseases such as SLE, antibodies or soluble IFNAR proteins that neutralize the action of this cytokine are being pursued as potential therapeutic approaches.

An alternative approach suggested for the treatment of type I IFN-dependent inflammatory diseases such as SLE is to use compounds that bind to cell surface molecules expressed by type I interferon expressing cells.

A class of compounds that have been studied for the treatment of autoimmune diseases are immunotoxins comprising a single chain Fv (scFv) from an antibody conjugated to a toxin. These compounds have been suggested to be useful for killing IL-3Rα expressing cells. However, these molecules suffer from numerous disadvantages. For example, immunotoxins are known to cause liver and kidney damage. The small size of a toxin conjugated to a scFv may also mean that the immunotoxin is rapidly cleared by the kidneys, further exacerbating damage to this organ and meaning that the immunotoxin may not be retained in the body for sufficient time to confer a benefit. Furthermore, the toxin component is generally non-human meaning that they can induce an immune response in a patient. This immune response can neutralize the molecule. Accordingly, such immunotoxins may not be amenable to multiple treatments, which may be required to treat a chronic autoimmune disease.

SUMMARY

Contrary to some previous approaches, the present inventors have realized that blocking type I IFN receptor and/or IFN-α may lack sufficient specificity to avoid compromising the positive, antiviral effects of type I IFNs. The present inventors instead focused on reducing or preventing the activity of IL-3 on IL-3 responsive cells and/or depleting or eliminating IL-3 responsive cells, such as pDCs and basophils. The present inventors made use of immunoglobulins against IL-3Rα to reduce or prevent the activity of IL-3 on IL-3 responsive cells (i.e., that neutralize IL-3 signaling), such as pDCs and basophils. However, the inventors found that immunoglobulins that only neutralize IL-3 signaling were unlikely to sufficiently reduce IFNα levels to provide a therapeutic benefit. Accordingly, the inventors made use of immunoglobulins additionally capable of inducing a mammal's immune system to at least partially deplete or eliminate IL-3 responsive cells (e.g., pDCs and basophils) to thereby treat type I IFN-dependent inflammatory diseases and conditions associated with pDCs and basophils, e.g., lupus. By using an immunoglobulin capable of both reducing or preventing the activity of IL-3 on IL-3 responsive cells and at least partially depleting or eliminating IL-3 responsive cells, the inventors were able to reduce IFNα levels in vitro. By using a mammal's immune system to at least partially deplete or eliminate IL-3 responsive cells, it is possible to avoid the use of toxins and the negative effects associated therewith.

Given that pDCs are not the only source of type I IFNs, but are an important source of type I IFNs in inflammatory disease, the inventors considered that the methods provided by the present disclosure provide a more precise, targeted therapeutic approach that is less likely to negate the positive effects of type I IFNs than methods directed at type I IFN receptor and/or IFN-α. A particular type I IFN-dependent inflammatory disease is lupus, e.g., SLE.

The inventors also found that immunoglobulins having an enhanced ability to induce antibody-dependent cell-mediated cytotoxicity (ADCC) were capable of reducing IFNα production and/or the number of circulating pDCs and basophils at a low dose. The inventors also found that these effects lasted for several days post administration and that the length of the effect is dose dependent.

The inventors also found that pDC and basophil numbers recover following administration of the immunoglobulin, meaning that a mammal's immune response (e.g., to virus) also recovers following treatment.

The present disclosure provides a method of treating lupus in a mammal, the method comprising administering to the mammal an immunoglobulin which binds an IL-3Rα chain and neutralizes IL-3 signaling and which depletes or at least partly eliminates pDCs and basophils to which it binds to thereby treat lupus in the mammal, wherein the immunoglobulin is not conjugated to a toxic compound that kills a cell to which the immunoglobulin binds. In one example, the lupus is SLE.

The present disclosure additionally or alternatively provides a method of treating lupus in a mammal, the method comprising administering to the mammal an immunoglobulin which binds an IL-3Rα chain and competitively inhibits the binding of monoclonal antibody 7G3 to IL-3Rα and which depletes or at least partly eliminates pDCs and basophils to which it binds to thereby treat lupus in the mammal. In one example, the immunoglobulin binds an IL-3Rα and neutralizes IL-3 signaling. In one example, the lupus is SLE.

The present disclosure additionally or alternatively provides a method of treating lupus in a mammal, the method comprising administering to the mammal an immunoglobulin which binds an IL-3Rα chain and competitively inhibits the binding of monoclonal antibody 7G3 to IL-3Rα and which depletes or at least partly eliminates pDCs and basophils to which it binds to thereby treat lupus in the mammal, wherein the immunoglobulin is not conjugated to a toxic compound that kills a cell to which the immunoglobulin binds. In one example, the immunoglobulin binds an IL-3Rα and neutralizes IL-3 signaling. In one example, the lupus is SLE.

The present disclosure also provides a method of treating Sjögrens syndrome in a mammal, the method comprising administering to the mammal an immunoglobulin which binds an IL-3Rα chain, wherein the immunoglobulin neutralizes IL-3 signaling and/or competitively inhibits the binding of monoclonal antibody 7G3 to IL-3Rα, and wherein the immunoglobulin depletes or at least partly eliminates pDCs and basophils to which it binds to thereby treat Sjögrens syndrome in the mammal, and wherein the immunoglobulin is not conjugated to a toxic compound that kills a cell to which the immunoglobulin binds.

The present disclosure also provides a method of treating scleroderma in a mammal, the method comprising administering to the mammal an immunoglobulin which binds an IL-3Rα chain, wherein the immunoglobulin neutralizes IL-3 signaling and/or competitively inhibits the binding of monoclonal antibody 7G3 to IL-3Rα, and wherein the immunoglobulin depletes or at least partly eliminates pDCs and basophils to which it binds to thereby treat systemic scleroderma in the mammal, wherein the immunoglobulin is not conjugated to a toxic compound that kills a cell to which the immunoglobulin binds. In one example, the scleroderma is systemic scleroderma.

In a further example, the present disclosure provides a pharmaceutical composition for use according to the aforementioned examples of the disclosure, the pharmaceutical composition comprising an immunoglobulin which binds an IL-3Rα chain and a pharmaceutically acceptable carrier, diluent or excipient. Exemplary immunoglobulins are described herein and apply to this example of the disclosure. In one example, the immunoglobulin is not conjugated to a toxic compound that kills a cell to which the immunoglobulin binds. In one example, the immunoglobulin depletes or at least partly eliminates pDCs and basophils to which it binds. In one example, the immunoglobulin binds an IL-3Rα and neutralizes IL-3 signaling. In one example, the immunoglobulin competitively inhibits the binding of monoclonal antibody 7G3 to IL-3Rα.

In a still further example, the present disclosure provides a kit for use according to the aforementioned examples of the disclosure, the kit comprising an immunoglobulin which binds an IL-3Rα chain; a pharmaceutically acceptable carrier, diluent or excipient; and instructions for use of the kit. Exemplary immunoglobulins that bind an IL-3Rα are described herein and are to be taken to apply mutatis mutandis to the present example of the disclosure.

In one example, the method comprises administering an amount of the immunoglobulin effective to neutralize IL-3 signaling and deplete or at least partly eliminate pDCs and basophils in the mammal.

In one example, the IL-3Rα is expressed by a pDC that produces one or more type I interferons. Accordingly, in one example, the immunoglobulin binds the IL-3Rα on a pDC that produces one or more type I interferons.

In one example, the IL3Rα chain is expressed by a basophil that produces one or more cytokines. Accordingly, in one example, the immunoglobulin binds the IL-3Rα on a basophil that produces one or more cytokines.

In one example, the immunoglobulin binds to the same epitope as monoclonal antibody 7G3.

In another example, the immunoglobulin binds to an epitope that overlaps with the epitope bound by monoclonal antibody 7G3.

In one example, the immunoglobulin specifically binds to the IL-3Rα.

In one example, the immunoglobulin is a naked immunoglobulin.

Exemplary immunoglobulins contemplated by the present disclosure are antibodies and antigen binding fragments thereof.

In one example, the immunoglobulin is a full length antibody.

In one example, the immunoglobulin is a chimeric immunoglobulin, e.g., a chimeric antibody or antigen binding fragment thereof. For example, the chimeric antibody comprises heavy chain variable regions ($V_H$s) and light chain variable regions ($V_L$s) from an antibody produced by a non-human mammal (e.g., a mouse) and constant regions from a human. In one example, the chimeric antibody comprises variable regions from monoclonal antibody 7G3.

In another example, the immunoglobulin is a humanized immunoglobulin, e.g., a humanized antibody or antigen binding fragment thereof. In one example, the humanized antibody or antigen binding fragment thereof is a humanized form of monoclonal antibody 7G3 or an antigen binding fragment thereof. For example, the humanized antibody comprises complementarity determining regions (CDRs) derived from monoclonal antibody 7G3. In one example, the humanized antibody comprises the CDRs of the $V_H$ of monoclonal antibody 7G3. In an additional or alternatively example, the humanized antibody comprises CDR2 and CDR3 of the $V_L$ of monoclonal antibody 7G3 and CDR1 of monoclonal 7G3 including one or more amino acid substitutions. In one example, the humanized antibody comprising a light chain variable region ($V_L$) comprising a sequence set forth in SEQ ID NO: 3 and a heavy chain variable region ($V_H$) comprising a sequence set forth in SEQ ID NO: 2.

In a further example, the immunoglobulin is a human immunoglobulin, such as a human antibody or antigen binding fragment thereof.

Exemplary antigen binding fragments contemplated by the present disclosure include:
(i) a domain antibody (dAb);
(ii) a Fv;
(iii) a scFv or stabilized form thereof (e.g., a disulfide stabilized scFv);
(iv) a dimeric scFv or stabilized form thereof);
(iv) a diabody, triabody, tetrabody or higher order multimer;
(v) Fab fragment;
(vi) a Fab' fragment;
(vii) a F(ab') fragment;
(viii) a F(ab')$_2$ fragment;
(ix) any one of (i)-(viii) fused to a Fc region of an antibody;
(x) any one of (i)-(viii) fused to an antibody or antigen binding fragment thereof that binds to an immune effector cell.

As will be apparent to the skilled artisan from the disclosure herein, exemplary immunoglobulins are capable of depleting or at least partly eliminating cells to which it binds without being conjugated to a toxic compound.

In one example, the immunoglobulin causes the cell to undergo apoptosis.

In one example, the immunoglobulin is capable of inducing an effector function, e.g., an effector function that results in killing a cell to which the immunoglobulin binds. Exemplary effector functions include ADCC, antibody-dependent cell-mediated phagocytosis (ADCP) and/or complement-dependent cytotoxicity (CDC).

In one example, the immunoglobulin is capable of inducing ADCC.

In one example, the immunoglobulin comprises an antibody Fc region capable of inducing an effector function. For example, the effector function is FC-mediated effector function. In one example, the Fc region is an IgG1 Fc region or an IgG3 Fc region or a hybrid IgG1/IgG2 Fc region.

In one example, the immunoglobulin is capable of inducing a similar (e.g., not significantly different or within about 10%) or the same level of effector function as a wild-type human IgG1 and/or human IgG3 Fc region.

In one example, the immunoglobulin is capable of inducing a similar (e.g., not significantly different or within about 10%) or the same level of effector function as ch7G3 or hz7G3 as described herein.

In one example, the immunoglobulin is capable of inducing an enhanced level of effector function.

In one example, the level of effector function induced by the immunoglobulin is enhanced relative to that of the immunoglobulin when it comprises a wild-type IgG1 Fc region.

In one example, the effector function is enhanced relative to, or greater than that of, ch7G3 or hz7G3 as described herein.

In one example the immunoglobulin is afucosylated or comprises a Fc region that is afucosylated.

In another example, the immunoglobulin has a lower level of fucosylation compared to an immunoglobulin produced by a human or a CHO cell that has not been altered to reduce the level of fucosylation of proteins. In accordance with this example, a lower level of fucosylation will be understood to mean that in a composition comprising the immunoglobulin the percentage of fucosylated immunoglobulins (e.g., glycosyl groups attached to Asn297 of an antibody comprising fucose) is lower than produced by a human or a CHO cell that has not been altered to reduce the level of fucosylation of proteins.

In one example, the immunoglobulin is hz7G3V3. For example, the immunoglobulin is an afucosylated humanized antibody comprising a light chain variable region ($V_L$) comprising a sequence set forth in SEQ ID NO: 3 and a heavy chain variable region ($V_H$) comprising a sequence set forth in SEQ ID NO: 2. For example, immunoglobulin is an afucosylated humanized antibody comprising a light chain comprising a sequence set forth in SEQ ID NO: 5 and a heavy chain comprising a sequence set forth in SEQ ID NO: 4.

In one example, the immunoglobulin is a humanized antibody comprising a light chain variable region ($V_L$) comprising a sequence set forth in SEQ ID NO: 3 and a heavy chain variable region ($V_H$) comprising a sequence set forth in SEQ ID NO: 2 expressed by a mammalian cell (e.g., a CHO cell) that does not express detectable levels of (or expresses reduced levels of) α-1,6-fucosyltransferase (FUT8). In one example, the immunoglobulin is an afucosylated humanized antibody comprising a light chain comprising a sequence set forth in SEQ ID NO: 5 and a heavy chain comprising a sequence set forth in SEQ ID NO: 4 expressed by a mammalian cell (e.g., a CHO cell) that does not express detectable levels of (or expresses reduced levels of) α-1,6-fucosyltransferase (FUT8).

In one example, the immunoglobulin comprises an Fc region comprising one or more amino acid sequence substitutions that enhance the effector function induced by the immunoglobulin. For example, the one or more amino acid sequence substitutions increase the affinity of the Fc region for a Fcγ receptor (FcγR) compared to a Fc region not comprising the substitutions. For example, the one or more amino acid substitutions enhance increase the affinity of the Fc region for a FcγR selected from the group consisting of FcγRI, FcγRIIa, FcγRIIc and FcγRIIIa compared to a Fc region not comprising the substitutions. In one example, the one or more amino acid sequence substitutions are:
(i) S239D, A330L and I332E according to the EU numbering system of Kabat; or
(ii) S239D and I332E according to the EU numbering system of Kabat.

For example, the immunoglobulin is a humanized antibody comprising a light chain variable region ($V_L$) comprising a sequence set forth in SEQ ID NO: 3 and a heavy chain variable region ($V_H$) comprising a sequence set forth in SEQ ID NO: 2, wherein the antibody comprises a Fc region comprising:
one or more amino acid sequence substitutions are:
(i) S239D, A330L and I332E according to the EU numbering system of Kabat; or
(ii) S239D and I332E according to the EU numbering system of Kabat.

In one example, the immunoglobulin is selected from the group consisting of: hz7G3V1 and hz7G3V2. For example, the immunoglobulin is an antibody comprising a light chain comprising a sequence set forth in SEQ ID NO: 5 and a heavy chain comprising a sequence set forth in SEQ ID NO: 6 (hz7G3V1) or comprising a light chain comprising a sequence set forth in SEQ ID NO: 5 and a heavy chain comprising a sequence set forth in SEQ ID NO: 7 (hz7G3V2).

In one example, following administration of the immunoglobulin to the mammal the number of pDCs and/or basophils in circulation in the mammal is reduced by at least about 50% compared to the number of the pDCs and/or basophils in circulation prior to administering the immunoglobulin.

For example, at least about six hours following administration of the immunoglobulin to the mammal, the number of pDCs and/or basophils in circulation in the mammal is reduced by at least about 50% compared to the number of the pDCs and/or basophils in circulation prior to administering the immunoglobulin.

For example, the number of pDCs and/or basophils in circulation in the mammal is reduced by at least about 50% compared to the number of pDCs and/or basophils in circulation prior to administering the immunoglobulin for at least 7 days post administration without further administrations of the immunoglobulin. For example, the number of pDCs and/or basophils in circulation in the mammal is reduced by at least about 50% compared to the number of pDCs and/or basophils in circulation prior to administering the immunoglobulin for at least 8 days or 10 days or 11 days or 15 days or 20 days or 21 days or 22 days or 28 days or 35 days or 42 days or 49 days or 50 days or 57 days or 60 days or 63 days or 70 days post administration without further administrations of the immunoglobulin.

For example, the number of pDCs and/or basophils in circulation in the mammal is reduced by at least about 50% or 55% or 60% or 65% or 70% or 75% or 80% or 85% or 90% or 95% or 96% or 97% or 98% or 99% compared to the number of the pDCs and/or basophils in circulation prior to administering the immunoglobulin.

In one example, the method comprises administering an effective amount of the immunoglobulin, such as a therapeutically effective amount of the immunoglobulin.

In one example, the method comprises administering between about 0.0001 mg/kg and 50 mg/kg of immunoglobulin to the mammal. For example, the method comprises administering between about 0.0005 mg/kg to about 50 mg/kg. For example, the method comprises administering between about 0.001 mg/kg to about 45 mg/kg. For example, the method comprises administering between about 0.005 mg/kg to about 40 mg/kg. For example, the method comprises administering between about 0.05 mg/kg to about 35 mg/kg. For example, the method comprises administering between about 0.1 mg/kg to about 30 mg/kg. For example, the method comprises administering between about 0.1 mg/kg to about 15 mg/kg. For example, the method comprises administering between about 0.1 mg/kg to about 10 mg/kg. For example, the method comprises administering between about 0.1 mg/kg to about 1 mg/kg. For example, the method comprises administering between about 10 mg/kg to about 30 mg/kg. For example, the method comprises administering between about 20 mg/kg to about 30 mg/kg.

In one example, the immunoglobulin is administered at a dose of 0.1 mg/kg.

In one example, the immunoglobulin is administered at a dose of 1 mg/kg.

In one example, the immunoglobulin is administered at a dose of 10 mg/kg.

In one example, the immunoglobulin is administered at a dose of 30 mg/kg.

In one example, the immunoglobulin is administered to the mammal a plurality of times. In one example, the period between administrations is at least about 7 days, such as at least about 8 days, for example, at least about 9 days or 10 days. In one example, the period between administrations is at least about 11 days. In another example, the period between administrations is at least about 15 days, such as at least about 16 days, for example, at least about 18 days or 20 days. In one example, the period between administrations is at least about 22 days. In another example, the period between administrations is at least about 25 days, such as at least about 30 days, for example, at least about 40 days or 45 days. In one example, the period between administrations is at least about 57 or 60 days.

For example, the immunoglobulin is administered at a dose of between 0.0001 mg/kg and 5 mg/kg, such as between 0.0005 mg/kg and 5 mg/kg, for example, between 0.001 mg/kg and 5 mg/kg, such as between 0.005 mg/kg and 5 mg/kg, and 5 mg/kg and the period between administrations is at least about 7 days or 8 days or 9 days or 10 days or 11 days. For example, the immunoglobulin is administered at a dose of between 0.01 mg/kg and 5 mg/kg and the period between administrations is at least about 7 days or 8 days or 9 days or 10 days or 11 days. For example, the immunoglobulin is administered at a dose of between 0.1 mg/kg and 2 mg/kg and the period between administrations is at least about 7 days or 8 days or 9 days or 10 days or 11 days. For example, the immunoglobulin is administered at a dose of between 0.1 mg/kg and 1 mg/kg and the period between administrations is at least about 7 days or 8 days or 9 days or 10 days or 11 days. In some examples, the period between administrations is at least about 7 days and less than about 22 days, such as at least about 11 days or 15 days and less than about 20 days, for example at least about 13 days and less than about 18 days.

In one example, the immunoglobulin is administered at a dose of 0.1 mg/kg and the period between administrations is 6 days or 7 days or 8 days or 9 days or 10 days or 11 days or 14 days or 15 days.

In one example, the immunoglobulin is administered at a dose of 1 mg/kg and the period between administrations is 6 days or 7 days or 8 days or 9 days or 10 days or 11 days or 14 days or 15 days or 20 days or 21 days or 22 days.

For example, the immunoglobulin is administered at a dose of between 6 mg/kg and 50 mg/kg and the period between administrations is at least about 15 days. For example, the immunoglobulin is administered at a dose of between 10 mg/kg and 30 mg/kg and the period between administrations is at least about 14 or 15 days. For example, the immunoglobulin is administered at a dose of between 20 mg/kg and 30 mg/kg and the period between administrations is at least about 14 or15 days. In some examples, the period between administrations is at least about 20 days and less than about 70 days, such as at least about 21 or 22 days and less than about 65 days, for example at least about 25 days and less than about 57 days.

In one example, the immunoglobulin is administered at a dose of 10 mg/kg and the period between administrations is 14 days or 15 days or 21 days or 22 days or 30 days or 48 days or 50 days or 56 days or 57 days or 60 days.

In one example, the immunoglobulin is administered at a dose of 30 mg/kg and the period between administrations is 14 days or 15 days or 21 days or 22 days or 30 days or 48 days or 50 days or 56 days or 57 days or 60 days.

In one example, the immunoglobulin is administered to a mammal suffering from lupus, e.g., SLE for a time and under conditions to reduce the level of circulating immune complexes and/or autoantibodies and/or inflammation or other symptom of lupus, e.g., SLE in the mammal (e.g., as described herein). In one example, the immunoglobulin is administered once or a plurality of times. If the immunoglobulin is administered a plurality of times, in some examples it is administered a sufficient number of times to significantly reduce the level of circulating immune complexes and/or autoantibodies and/or inflammation or other symptom of lupus, e.g., SLE in the mammal (e.g., as described herein). In some examples, the immunoglobulin is re-administered when the level of circulating immune complexes and/or autoantibodies and/or inflammation or other symptom of lupus, e.g., SLE in the mammal (e.g., as described herein) is no longer significantly reduced.

In some examples, if the immunoglobulin is administered a plurality of times it is administered a sufficient number of times to reduce the level of circulating immune complexes and/or autoantibodies and/or inflammation or other symptom of lupus, e.g., SLE in the mammal (e.g., as described herein) to a level similar to (e.g., within 10% or 20%) of a healthy subject. In some examples, the immunoglobulin is re-administered when the level of circulating immune complexes and/or autoantibodies and/or inflammation or other symptom of lupus, e.g., SLE in the mammal (e.g., as described herein) is no longer significantly reduced.

In one example, the method additionally comprises detecting the level of circulating immune complexes and/or autoantibodies and/or inflammation or other symptom of lupus, e.g., SLE in the mammal and if the level is not reduced repeating administration of the immunoglobulin.

In one example, the level of circulating immune complexes and/or autoantibodies and/or inflammation or other symptom of lupus, e.g., SLE in the mammal is reduced to a level detected in a healthy mammal.

In one example, the method additionally comprises detecting the number of pDCs and/or basophils in circulation and/or in an inflamed tissue in the mammal.

In one example, the method additionally comprises repeating administration of the immunoglobulin if the number of pDCs and/or basophils detected in circulation is within about 50% of the number of pDCs and/or basophils in circulation prior to administering the immunoglobulin. For example, the method additionally comprises repeating administration of the immunoglobulin if the number of pDCs and/or basophils detected in circulation is within about 60%, 70%, 75%, 80%, 85%, 90% or 95% of the number of pDCs and/or basophils in circulation prior to administering the immunoglobulin.

In one example, after administration of the immunoglobulin has ceased, the number of pDCs and/or basophils in circulation in the subject increase. For example, the number of pDCs and/or basophils in circulation in the subject increase to a level similar to the level in a normal or healthy subject and/or in a population of normal or healthy subjects. For example, the number of pDCs and/or basophils in circulation in the subject increase after about 11 days or 20 days 22 days or 30 days or 57 days or 60 days or 65 days or 70 days following ceasing treatment.

The present disclosure also provides a method for preventing a relapse of lupus, e.g., SLE in a mammal, the method comprising administering an immunoglobulin as described herein according to any example to a mammal undergoing a relapse of lupus, e.g., SLE or at risk of developing a relapse of lupus, e.g., SLE to thereby preventing the relapse of lupus, e.g., SLE.

In one example, the method comprises administering an effective amount of the immunoglobulin, such as a prophylactically effective amount of the immunoglobulin.

In one example, the method additionally comprises identifying a mammal undergoing a relapse of lupus, e.g., SLE. For example, the method comprises detecting autoantibodies (e.g., against C1q) and/or anti-dsDNA antibodies and/or immune complexes in circulation of the mammal. Methods for determining a mammal undergoing a relapse of lupus, e.g., SLE are known in the art and/or described herein.

In one example, the immunoglobulin is administered as described herein according to any example of the present disclosure.

In one example, a mammal to be treated is in need of such treatment. For example, the mammal suffers from the disease or condition or is at risk of developing the disease or condition or is undergoing a relapse of the disease or condition or at risk of relapsing. In one example, the mammal in need of treatment has an increased level of IFNα in circulation, e.g., compared to the level detected in a population of healthy mammals.

Suitably, according to the aforementioned examples of the present disclosure, the mammal is a human.

Other objects, examples and advantages will become apparent from the following detailed description. The detailed description and specific examples are given for illustration only since various changes and modifications within the spirit and scope of the present disclosure will become apparent to those skilled in the art from this detailed description. Further, the examples demonstrate the principle of methods disclosed in the present disclosure and do not specifically illustrate the application of the present disclosure to all the examples where it will be obviously useful to those skilled in the prior art.

DETAILED DESCRIPTION

Key to Sequence Listing

Figure 1:
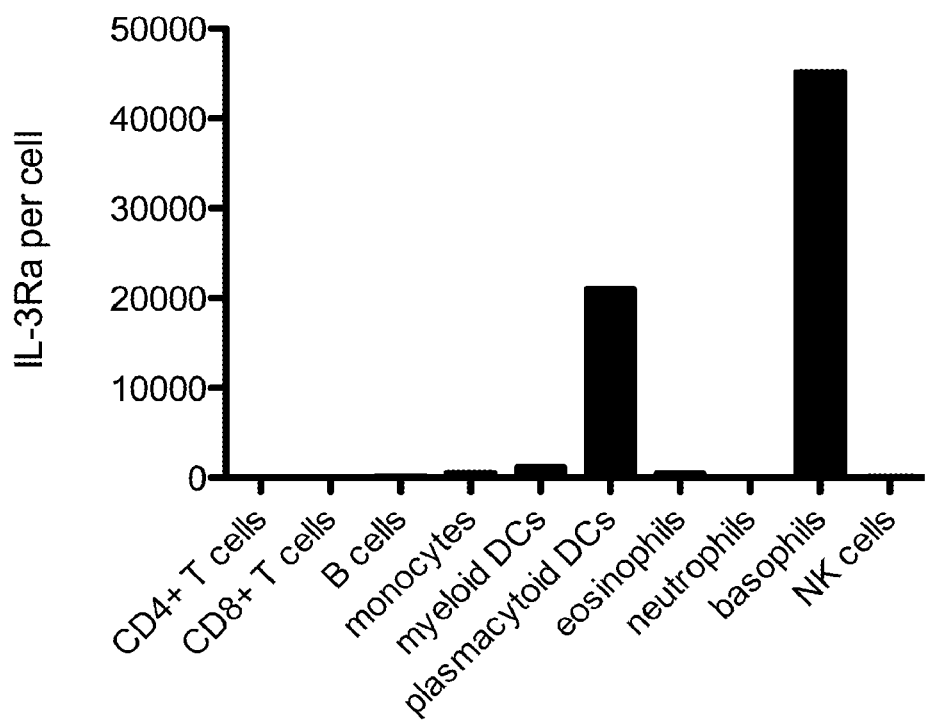
FIG. 1 is a graphical representation showing the average level of expression of IL-3Rα per cell (Y-axis) in various cell lineages (X-axis).

SEQ ID NO: 1 is an amino acid sequence of a IL-3Rα chain.
SEQ ID NO: 2 is an amino acid sequence of a $V_H$ of hz7G3.
SEQ ID NO: 3 is an amino acid sequence of a $V_L$ of hz7G3.
SEQ ID NO: 4 is an amino acid sequence of a heavy chain of hz7G3.
SEQ ID NO: 5 is an amino acid sequence of a light chain of hz7G3.
SEQ ID NO: 6 is an amino acid sequence of a heavy chain of hz7G3V1.
SEQ ID NO: 7 is an amino acid sequence of a heavy chain of hz7G3V2.

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter.

Those skilled in the art will appreciate that the present disclosure is susceptible to variations and modifications other than those specifically described. It is to be understood that the disclosure includes all such variations and modifications. The disclosure also includes all of the steps, features, compositions and compounds referred to or indicated in this specification, individually or collectively, and any and all combinations or any two or more of said steps or features.

The present disclosure is not to be limited in scope by the specific examples described herein, which are intended for the purpose of exemplification only. Functionally-equivalent products, compositions and methods are clearly within the scope of the present disclosure.

Any example of the present disclosure herein shall be taken to apply mutatis mutandis to any other example of the disclosure unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Selected Definitions

As used herein, the term "immunoglobulin" includes any antigen-binding protein product of the immunoglobulin gene complex, including immunoglobulin isotypes IgA, IgD, IgM, IgG and IgE and antigen-binding fragments thereof. Exemplary immunoglobulins are antibodies. The immunoglobulin may be polyclonal or monoclonal, with monoclonals being one exemplary form of the disclosure. Included in the term "immunoglobulin" are any immunoglobulins that are appropriately de-immunized to thereby reduce or eliminate an immune response by a mammal to an immunoglobulin that has been administered to the mammal. In the particular case of treatment of humans, suitable immunoglobulins include chimeric, humanized or human immunoglobulins. Also included within the term "immunoglobulin" are modified, mutagenized, chimeric and/or humanized immunoglobulins that comprise altered or variant amino acid residues, sequences or glycosylation, whether naturally occurring or produced by human intervention (e.g. by recombinant DNA technology). The skilled addressee will appreciate that the "immunoglobulins" of the present disclosure may be substituted with other binding moieties and/or sequences based on alternate immunoglobulin or non-immunoglobulin protein scaffolds which have been adapted to bind to the IL-3Rα chain. Exemplary proteins include an Fc receptor binding portion. For example, proteins encompassed by the term "immunoglobulin" include domain antibodies, camelid antibodies and antibodies from cartilaginous fish (i.e., immunoglobulin new antigen receptors (IgNARs)). Generally, camelid antibodies and IgNARs comprise a $V_H$, however lack a $V_L$ and are often referred to as heavy chain immunoglobulins. Other "immunoglobulins" include T cell receptors and other immunoglobulin-like domain containing proteins that are capable of binding to an antigen, e.g., by virtue of an antigen binding site comprising a variable region.

The skilled artisan will be aware that an "antibody" is generally considered to be a protein that comprises a variable region made up of a plurality of polypeptide chains, e.g., a polypeptide comprising a $V_L$ and a polypeptide comprising a $V_H$. An antibody also generally comprises constant domains, some of which can be arranged into a constant region or constant fragment or fragment crystallizable (Fc). A $V_H$ and a $V_L$ interact to form a Fv comprising an antigen binding region that is capable of specifically binding to one or a few closely related antigens. Generally, a light chain from mammals is either a κ light chain or a λ light chain and a heavy chain from mammals is α, δ, ε, γ, or μ. Antibodies can be of any type (e.g., IgG, IgE, IgM, IgD, IgA, and IgY), class (e.g., $IgG_1$, $IgG_2$, $IgG_3$, $IgG_4$, $IgA_1$ and $IgA_2$) or subclass. The term "antibody" also encompasses humanized antibodies, primatized antibodies, human antibodies and chimeric antibodies.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof. In some cases, the intact antibody may have one or more effector functions.

An "antigen binding fragment" of an antibody comprises the antigen binding and/or the variable region of the intact antibody. Examples of antibody fragments include Fab, Fab', F(ab')$_2$ and Fv fragments; diabodies; linear antibodies; single-chain antibody molecules and multispecific antibodies formed from antibody fragments.

In the context of the present disclosure, "effector functions" refer to those biological activities mediated by cells or proteins that bind to the Fc region (a native sequence Fc region or amino acid sequence variant Fc region) of an antibody that result in killing of a cell. Examples of effector functions induced by antibodies include: complement dependent cytotoxicity; antibody-dependent-cell-mediated cytotoxicity (ADCC); antibody-dependent-cell-phagocytosis (ADCP); and B-cell activation. In the context of the present disclosure, the term "effector function induced by an immunoglobulin" or like term is used interchangeable with "effector function of an immunoglobulin" or like term and each provides literal support for the other.

"Antibody-dependent-cell-mediated cytotoxicity" or "ADCC" refers to a form of cytotoxicity in which secreted Ig bound onto Fc receptors ("FcRs") present on certain cytotoxic cells (e.g., natural killer ("NK") cells, neutrophils and macrophages) enable these cytotoxic effector cells to bind specifically to an antigen-bearing target-cell and subsequently kill the target-cell with cytotoxins. To assess ADCC activity of a molecule of interest, an in vitro ADCC assay may be performed. Useful effector cells for such assays include peripheral blood mononuclear cells ("PBMC") and NK cells.

As used herein, "variable region" refers to the portions of the light and/or heavy chains of an antibody as defined herein that is capable of specifically binding to an antigen and, for example, includes amino acid sequences of CDRs; i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain. The amino acid positions assigned to CDRs and FRs can be defined according to Kabat (1987 and 1991, supra) or other numbering systems in the performance of methods according to the present disclosure, e.g., the hypervariable loop numbering system of Clothia and Lesk (1987 and/or 1989, supra and/or Al-Lazikani et al., 1997, supra). For example, according to the numbering system of Kabat, a $V_H$ FRs and CDRs positioned as follows residues 1-30 (FR1), 31-25 (CDR1), 36-49 (FR2), 50-65 (CDR2), 66-94 (FR3), 95-102 (CDR3) and 103-113 (FR4), numbered according to the Kabat numbering system. For example, according to the numbering system of Kabat, a $V_L$ FRs and CDRs are positioned as follows residues 1-23 (FR1), 24-34 (CDR1), 35-49 (FR2), 50-56 (CDR2), 57-88 (FR3), 89-97 (CDR3) and 98-107 (FR4).

As used herein, the term "complementarity determining regions" (syn. CDRs; i.e., CDR1, CDR2, and CDR3) refers to the amino acid residues of an antibody variable domain that form loops between the FRs the sequence of which vary between antibodies. Some or all of the CDRs confer the ability to bind antigen on the antibody. Each variable domain typically has three CDR regions identified as CDR1, CDR2 and CDR3. Each complementarity determining region may comprise amino acid residues from a "complementarity determining region" as defined by Kabat et al., (1991) and/or those residues from a "hypervariable loop" Chothia and Lesk (1987), or any other known numbering technique or combination thereof, including the IMGT numbering system (Le Franc et al., 2003).

"Framework regions" (hereinafter FR) are those variable domain residues other than the CDR residues.

The term "constant region" or "fragment crystalizable" or "Fc" or "Fc region" or "Fc portion" (which can be used interchangeably herein) as used herein, refers to a portion of an antibody comprising at least one constant domain and which is generally (though not necessarily) glycosylated and which is capable of binding to one or more Fc receptors and/or components of the complement cascade. The heavy chain constant region can be selected from any of the five isotypes: α, δ, ε, γ, or μ. Furthermore, heavy chains of various subclasses (such as the IgG subclasses of heavy chains) are responsible for different effector functions and thus, by choosing the desired heavy chain constant region, proteins with desired effector function can be produced. Exemplary heavy chain constant regions are gamma 1 (IgG1), gamma 2 (IgG2) and gamma 3 (IgG3), or hybrids thereof.

A "constant domain" is a domain in an antibody the sequence of which is highly similar in antibodies/antibodies of the same type, e.g., IgG or IgM or IgE. A constant region of an antibody generally comprises a plurality of constant domains, e.g., the constant region of γ, α and δ heavy chains comprises two constant domains.

As used herein, the term "specifically binds" shall be taken to mean an immunoglobulin reacts or associates more frequently, more rapidly, with greater duration and/or with greater affinity with IL-3Rα or cell expressing same than it does with alternative antigens or cells. It is also understood by reading this definition that, for example, an immunoglobulin specifically binds to IL-3Rα may or may not specifically bind to a second antigen. As such, "specific binding" does not necessarily require exclusive binding or non-detectable binding of another antigen. The term :specifically binds" is used interchangeably with "selectively binds" herein. Generally, reference herein to binding means specific binding, and each term shall be understood to provide explicit support for the other term.

The term "competitively inhibits" shall be understood to mean that an immunoglobulin reduces or prevents binding of the monoclonal antibody designated 7G3 to IL-3Rα. It will be apparent from the foregoing that the immunoglobulin need not completely inhibit binding of the monoclonal antibody 7G3, rather it need only reduce binding by a statistically significant amount, for example, by at least about 10% or 20% or 30% or 40% or 50% or 60% or 70% or 80% or 90% or 95%. Methods for determining competitive inhibition of binding are known in the art and/or described herein. For example, monoclonal antibody 7G3 is exposed to IL-3Rα either in the presence or absence of the immunoglobulin. If less monoclonal antibody binds in the presence of the immunoglobulin than in the absence of the immunoglobulin, the immunoglobulin is considered to competitively inhibit binding of monoclonal antibody 7G3.

By "overlapping" in the context of two epitopes shall be taken to mean that two epitopes share a sufficient number of amino acid residues to permit an immunoglobulin that binds to one epitope to competitively inhibit the binding of an immunoglobulin that binds to the other epitope. For example, the two epitopes share at least 1 or 2 or 3 or 4 or 5 or 6 or more amino acids.

As used herein, the term "neutralize" shall be taken to mean that an immunoglobulin is capable of reducing or preventing IL-3-mediated signaling in a cell and/or reducing or preventing IL-3 binding to IL-3Rα chain and/or a heterodimer of IL-3Rα chain and IL-3Rβ chain (also known as colony stimulating factor 2 receptor).

Reference herein to "monoclonal antibody 7G3" or to "7G3" is a reference to the monoclonal antibody produced by the hybridoma designated 7G3 as deposited with the ATCC under accession number HB-12009 and described in U.S. Pat. No. 6,177,078. Monoclonal antibody 7G3 is also commercially available, e.g., from BD Biosciences (NJ, USA).

The term "EU numbering system of Kabat" will be understood to mean the numbering of an immunoglobulin heavy chain is according to the EU index as taught in Kabat et al., 1991, Sequences of Proteins of Immunological Interest, 5th Ed., United States Public Health Service, National Institutes of Health, Bethesda. The EU index is based on the residue numbering of the human IgG1 EU antibody.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease (e.g., lupus) are mitigated or eliminated.

As used herein, the term "prevention" includes providing prophylaxis with respect to occurrence or recurrence of a disease in an individual. An individual may be predisposed to or at risk of developing the disease or disease relapse but has not yet been diagnosed with the disease or the relapse.

As used herein, a mammal "at risk" of developing a disease or condition or relapse thereof (e.g. SLE) or relapsing may or may not have detectable disease or symptoms of disease, and may or may not have displayed detectable disease or symptoms of disease prior to the treatment according to the present disclosure. "At risk" denotes that a mammal has one or more risk factors, which are measurable parameters that correlate with development of the disease or condition, as known in the art and/or described herein.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is meant an amount necessary to effect treatment of a disease or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner.

The effective amount can be administered in a single dose or in a dose repeated once or several times over a treatment period.

A "therapeutically effective amount" is at least the minimum concentration required to effect a measurable improvement of a particular disorder (e.g., SLE). A therapeutically effective amount herein may vary according to factors such as the disease state, age, sex, and weight of the patient, and the ability of the immunoglobulin to elicit a desired response in the individual. A therapeutically effective amount is also one in which any toxic or detrimental effects of the immunoglobulin are outweighed by the therapeutically beneficial effects.

A "prophylactically effective amount" refers to an amount effective, at the dosages and for periods of time necessary, to achieve the desired prophylactic result. Typically but not necessarily, since a prophylactic dose is used in mammals prior to or at an earlier stage of disease, a prophylactically effective amount may be less than a therapeutically effective amount.

As used herein, a "plasmacytoid dendritic cell" or "pDC" is a type of circulating dendritic cell found in the blood peripheral lymphoid organs that produces type I interferons, such as, IFNα and IFNβ. Human pDCs express the surface markers IL-3Rα, BDCA-2 (CD303), BDCA-4 (CD304) and toll-like receptors 7 and 9. Generally, human pDC do not express CD11c or CD14. A typical human pDC surface phenotype is $CD20^-$, $CD3^-$ $CD14^-$, $CD19^-$ $CD56^-$, $HLA^-DR^+$, $CD11c^-$ and $CD123^-$.

As used herein, a "basophil" is a rare type of granulocyte that produces various cytokines (e.g., IL-4, IL-6, IL-13), histamine and leukotrines. Human basophils express cell surface markers, such as, IL-3Rα, FcϵR1, CD49b, CD69 or CD203.

The term "naked antibody" refers to an antibody that is not conjugated to another compound, e.g., a toxic compound or radiolabel.

For the purposes of nomenclature only and not limitation, the amino acid sequence of an IL-3Rα chain is taught in Gene ID Accession Number 3563 and/or in SEQ ID NO: 1.

The "mammal" treated according to the present disclosure may be a primate, livestock (e.g. sheep, horses, cattle, pigs, donkeys), companion animal (e.g. pets such as dogs and cats), laboratory test animal (e.g. mice, rabbits, rats, guinea pigs), performance animal (e.g. racehorses, camels, greyhounds) or captive wild animal. In one example, the mammal is a human.

Immunoglobulins

Exemplary immunoglobulins suitable for use in a method of the present disclosure are described herein and the following paragraphs describe additional exemplary immunoglobulins.

In one example, the immunoglobulin is capable of reducing IFNα secretion from PBMC that have been contacted with an inducer of IFNα secretion. For example, the PBMC are exposed to a toll like receptor (TLR)-7/9 agonist, such as a CpG oligonucleotide, e.g., a type C CpG oligonucleotide. For example, the cells contacted with a type C CpG oligonucleotide at a concentration of 1 µM or 2 µM or 3 µM or 4 µM or 5 µM. In one example, the level of IFNα is reduced compared to the level in the absence of the immunoglobulin or in the presence of an isotype control immunoglobulin (e.g., that does not bind IL-3Rα). In one example, the level of IFNα is reduced by about 50% or at least 60% or at least 70% or at least 80% or at least 90%. For example, the immunoglobulin is capable of achieving the reduction in IFNα at a concentration of between 0.01 µg/ml to about 15 µg/ml, such as between 0.04 µg/ml to about 4 µg/ml, for example, between 0.1 µg/ml to about 1 µg/ml.

In another example, the immunoglobulin is capable of reducing the number of pDCs and/or basophils detectable in a population of PBMC. In one example, the number of pDCs and/or basophils is reduced compared to the level in the absence of the immunoglobulin or in the presence of an isotype control immunoglobulin (e.g., that does not bind IL-3Rα). In one example, the number of pDCs and/or basophils is reduced by about 50% or at least 60% or at least 70% or at least 80% or at least 90%. In one example, the immunoglobulin is capable of reducing the number of pDCs and/or basophils within 4 hours after contacting the PBMC with the immunoglobulin, or within 24 hours after contacting the PBMC with the immunoglobulin or within 48 hours after contacting the PBMC with the immunoglobulin.

In a further example, the immunoglobulin is capable of reducing the number of basophils and/or pDCs in circulation of a mammal (e.g., a non-human primate, such as a cynomolgous monkey) for at least 7 days following a single administration at a dose of no more than 2 mg/kg, e.g., a dose of no more than 1 mg/kg or a dose of no more than 0.1 mg/kg. For example, the number of basophils and/or pDCs is reduced to less than 70% (or 80% or 90% or 95%) of the number of the cells prior to administration of the immunoglobulin. In one example, the number of cells is calculated as a percentage of total cells in peripheral blood. For example, the cells are reduced for at least 8 days or 10 days or 11 days. For example, the number of pDCs is reduced for at least 8 days or 9 days or 10 days or 11 days or 12 days or 13 days or 14 days or 15 days. In one example the number of pDCs is reduced for at least 11 days. For example, the number of basophils is reduced for at least 5 days or 6 days or 7 days or 8 days or 9 days or 10 days. In one example, the number of basophils is reduced for at least 8 days.

In a further example, the immunoglobulin is capable of reducing the number of basophils and/or pDCs in circulation of a mammal (e.g., a non-human primate, such as a cynomolgous monkey) for at least 15 days following a single administration at a dose of no more than 40 mg/kg, e.g., a dose of no more than 30 mg/kg or a dose of no more than 10 mg/kg. For example, the number of basophils and/or pDCs is reduced to less than 70% (or 80% or 90% or 95%) of the number of the cells prior to administration of the immunoglobulin. In one example, the number of cells is calculated as a percentage of total cells in peripheral blood. For example, the cells are reduced for at least 21 days or 22 days or 30 days or 35 days or 40 days or 49 days or 50 days or 57 days or 63 days or 65 days or 70 days. For example, the number of pDCs is reduced for at least 12 days or 13 days or 14 days or 15 days or 16 days or 17 days or 18 days or 19 days or 20 days. In one example the number of pDCs is reduced for at least 15 days. For example, the number of basophils is reduced for at least 12 days or 13 days or 14 days or 15 days or 16 days or 17 days or 18 days or 19 days or 20 days or 21 days or 22 days or 23 days or 24 days or 25 days or 26 days or 27 days or 28 days. In one example, the number of basophils is reduced for at least 15 days (e.g., following a 10 mg/kg dose) or 22 days (e.g., following a 30 mg/kg dose).

In one example, the immunoglobulin does not reduce or deplete the number of neutrophils and/or T cells and/or B cells and/or monocytes and/or red blood cells when administered a mammal (e.g., a non-human primate, such as a cynomolgous monkey). For example, the immunoglobulin does not reduce or deplete the number of neutrophils and/or T cells and/or B cells and/or monocytes and/or red blood cells by more than about 10% or 20% or 30% or 40% or 50% or by a statistically significant amount compared to the level(s) prior to administration of the immunoglobulin. For example, the immunoglobulin does not induce death of neutrophils and/or T cells and/or B cells and/or monocytes and/or red blood cells Antibodies In one example, an immunoglobulin as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods an IL-3Rα protein or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the scrum isolated and stored, and/or the animal is used to generate monoclonal antibodies (Mabs).

Monoclonal antibodies are one exemplary form of antibody contemplated by the present disclosure. The term "monoclonal antibody" or "MAb" refers to a homogeneous antibody population capable of binding to the same antigen(s), for example, to the same epitope within the antigen. This term is not intended to be limited as regards to the source of the antibody or the manner in which it is made.

For the production of Mabs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human immunoglobulin proteins and, for example, do not express murine immunoglobulin proteins, can also be used to generate an antibody of the present disclosure (e.g., as described in WO2002/066630).

Following immunization, somatic cells with the potential for producing antibodies, specifically B lymphocytes (B cells), are selected for use in the MAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods*. 197: 85-95, 1996).

Antibodies can also be produced or isolated by screening a display library, e.g., a phage display library, e.g., as described in U.S. Pat. No. 6,300,064 and/or U.S. Pat. No. 5,885,793.

In one example, the antibody is 7G3, 6H6 or 9F5 as described in U.S. Pat. No. 6,177,078. Modified versions (e.g., de-immunized, chimeric or humanized versions, such as by methods described herein) of these antibodies are also contemplated.

Chimeric Antibodies

The immunoglobulin may be a synthetic immunoglobulin. In one example an antibody described herein is a chimeric antibody. The term "chimeric antibody" refers to antibodies in which a portion of the heavy and/or light chain is identical with or homologous to corresponding sequences in antibodies derived from a particular species (e.g., murine, such as mouse) or belonging to a particular antibody class or subclass, while the remainder of the chain(s) is identical with or homologous to corresponding sequences in antibodies derived from another species (e.g., primate, such as human) or belonging to another antibody class or subclass. Typically chimeric antibodies utilize rodent or rabbit variable regions and human constant regions, in order to produce an antibody with predominantly human domains. Methods for producing chimeric antibodies are described in, e.g., U.S. Pat. No. 4,816,567; and U.S. Pat. No. 5,807,715.

The present disclosure also includes a chimeric immunoglobulin, e.g., in which a variable region from one species is fused to a region of a protein from another species. For example, the disclosure contemplates an immunoglobulin comprising a variable region from a T cell receptor of one species fused to a T cell receptor constant domain from a separate species.

Humanized and Human Antibodies

The antibodies of the present disclosure may be humanized or human.

The term "humanized antibody" shall be understood to refer to a subclass of chimeric antibodies having an antigen binding site or variable region derived from an antibody from a non-human species and the remaining antibody structure of the molecule based upon the structure and/or sequence of a human antibody. The antigen-binding site comprises the complementarity determining regions (CDRs) from the non-human antibody grafted onto appropriate FRs in the variable domains of a human antibody and the remaining regions from a human antibody. Antigen binding sites may be wild type or modified by one or more amino acid substitutions. In some instances, FR residues of the human immunoglobulin are replaced by corresponding non-human residues.

Methods for humanizing non-human antibodies or parts thereof (e.g., variable regions) are known in the art. Humanization can be performed following the method of U.S. Pat. No. 5,225,539, or U.S. Pat. No. 5,585,089. Other methods for humanizing an antibody are not excluded.

The term "human antibody" as used herein in connection with antibodies refers to antibodies having variable regions (e.g. $V_H$, $V_L$) and, optionally constant regions derived from or corresponding to sequences found in humans, e.g. in the human germline or somatic cells. The "human" antibodies can include amino acid residues not encoded by human sequences, e.g. mutations introduced by random or site directed mutations in vitro (in particular mutations which involve conservative substitutions or mutations in a small number of residues of the antibody, e.g. in 1, 2, 3, 4 or 5 of the residues of the antibody, e.g. in 1, 2, 3, 4 or 5 of the residues making up one or more of the CDRs of the antibody). These "human antibodies" do not actually need to be produced by a human, rather, they can be produced using recombinant means and/or isolated from a transgenic animal (e.g., mouse) comprising nucleic acid encoding human antibody constant and/or variable regions (e.g., as described above). Human antibodies can be produced using various techniques known in the art, including phage display libraries (e.g., as described in U.S. Pat. No. 5,885,793).

Human antibodies which recognize a selected epitope can also be generated using a technique referred to as "guided selection." In this approach a selected non-human monoclonal antibody, e.g., a mouse antibody, is used to guide the selection of a completely human antibody recognizing the same epitope (e.g., as described in U.S. Pat. No. 5,565,332).

De-Immunized Antibodies and Immunoglobulins

The present disclosure also contemplates a de-immunized antibody or protein. De-immunized antibodies and proteins have one or more epitopes, e.g., B cell epitopes or T cell epitopes removed (i.e., mutated) to thereby reduce the likelihood that a mammal will raise an immune response against the antibody or protein. Methods for producing de-immunized antibodies and proteins are known in the art and described, for example, in WO00/34317, WO2004/108158 and WO2004/064724.

Methods for introducing suitable mutations and expressing and assaying the resulting protein will be apparent to the skilled artisan based on the description herein.

Heavy Chain Antibodies

Heavy chain antibodies differ structurally from many other forms of antibodies, in so far as they comprise a heavy chain, but do not comprise a light chain. Accordingly, these immunoglobulins are also referred to as "heavy chain only antibodies". Heavy chain immunoglobulins are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain immunoglobulins from cartilaginous fish and the variable regions thereof and methods for their production and/or isolation and/or use is found inter alia in WO2005/118629.

Antibody Fragments

Single-Domain Antibodies

In some examples, an immunoglobulin of the disclosure is or comprises a single-domain antibody (which is used interchangeably with the term "domain antibody" or "dAb"). A single-domain antibody is a single polypeptide chain comprising all or a portion of the heavy chain variable domain of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies

In some examples, an immunoglobulin of the disclosure is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding site, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

A diabody, triabody, tetrabody, etc capable of inducing effector activity can be produced using an antigen binding domain capable of binding to IL-3Rα and an antigen binding domain capable of binding to a cell surface molecule on an immune cell, e.g., a T cell (e.g., CD3).

Single Chain Fv (scFv) Fragments

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present disclosure also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present disclosure encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

The present disclosure also contemplates a dimeric scFv capable of inducing effector activity. For example, one scFv binds to IL-3Rα and another scFv binds to a cell surface molecule on an immune cell, e.g., a T cell (e.g., CD3). In one example, the dimeric protein is a combination of a dAb and a scFv. Examples of bispecific antibody fragments capable of inducing effector function are described, for example, in U.S. Pat. No. 7,235,641.

Other Antibodies and Antibody Fragments

The present disclosure also contemplates other antibodies and antibody fragments, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Fc Regions

The present disclosure encompasses immunoglobulins comprising a Fc region of an antibody, including antigen binding fragments of an immunoglobulin fused to a Fc.

Sequences of Fc regions useful for producing the proteins of the present disclosure may be obtained from a number of different sources. In some examples, the Fc or portion thereof of the protein is derived from a human antibody. Moreover, the Fc or portion thereof may be derived from any antibody class, including IgM, IgG, IgD, IgA and IgE, and any antibody isotype, including IgG1, IgG2, IgG3 and IgG4. In one example, the Fc is human isotype IgG1 or human isotype IgG2 or human isotype IgG3 or a hybrid of any of the foregoing.

In one example, the Fc region is capable of inducing an effector function. For example, the Fc region is a human IgG1 or IgG3 Fc region. In another example, the Fc region is a hybrid of an IgG1 and an IgG2 Fc region or a hybrid of an IgG1 and an IgG3 Fc region or a hybrid of an IgG2 and an IgG3 Fc region. Exemplary hybrids of human IgG1 and IgG2 Fc regions are described in Chappel et al., *Proc. Natl Acad. Sci. USA*, 88: 9036-9040, 1991.

Methods for determining whether or not a Fc region can induce effector function will be apparent to the skilled artisan and/or described herein.

Effector Function

Suitably, an anti-IL-3Rα immunoglobulin suitable for use in the methods of the present disclosure has or displays an effector function that facilitates or enables at least partial depletion, substantial depletion or elimination of IL-3Rα+ plasmacytoid dendritic cells. Such an effector function may be enhanced binding affinity to Fc receptors, antibody-dependent cell-mediated cytotoxicity (ADCC), antibody-dependent cell mediated phagocytosis (ADCP) and/or complement dependent cytotoxicity (CDC).

As will be apparent to the skilled artisan based on the description herein, some examples of the present disclosure make use of an immunoglobulin capable of inducing effector function.

In one example, the immunoglobulin binds to IL-3Rα in such a manner that it is capable of inducing an effector function, such as, ADCC.

In one example, the immunoglobulin binds to an epitope within IL-3Rα that permits it to induce an effector function, such as ADCC.

In another example, the immunoglobulin is capable of binding to IL-3Rα on a pDC and/or a basophil in a mammal to thereby induce an effector function, such as ADCC.

For example, the immunoglobulin remains bound to IL-3Rα on the surface of the cell for a time sufficient to induce an effector function, such as ADCC. For example, the immunoglobulin is not internalized too quickly to permit ADCC to be induced.

Alternatively, or in addition, the immunoglobulin is bound to the IL-3Rα on the surface of the cell in a manner permitting an immune effector cell to bind to a Fc region in the immunoglobulin and induce an effector function, such as ADCC. For example, the Fc region of the immunoglobulin is exposed in such a manner when the immunoglobulin is bound to the IL-3Rα that is capable of interacting with a Fc receptor (e.g., a FcγR) on an immune effector cell. In the context of the present disclosure, the term "immune effector cell" shall be understood to mean any cell that expresses a Fc receptor and that is capable of killing a cell to which it is bound by ADCC or ADCP.

Each of the above paragraphs relating to effector functions of an immunoglobulin shall be taken to apply mutatis mutandis to inducing CDC. For example, the immunoglobulin is bound to the IL-3Rα on the surface of the cell in a manner permitting complement component C1q to bind to a Fc region in the immunoglobulin and induce CDC.

In one example, the immunoglobulin is capable of inducing an enhanced level of effector function.

In one example, the level of effector function induced by the Fc region is enhanced relative to a wild-type Fc region of an IgG1 antibody or a wild-type Fc region of an IgG3 antibody.

In another example, the Fc region is modified to increase the level of effector function it is capable of inducing compared to the Fc region without the modification. Such modifications can be at the amino acid level and/or the secondary structural level and/or the tertiary structural level and/or to the glycosylation of the Fc region.

In one example, an anti-IL-3Rα immunoglobulin has or displays a level of effector function that is greater than that exhibited by ch7G3 (a chimeric version of 7G3 comprising a wild-type human IgG1 Fc region, referred to as CSL360 in International Publication WO2009/070844) or hz7G3 (a humanized version of 7G3 comprising a wild-type human IgG1 Fc region). In the context of the present disclosure ch7G3 and hz7G3 exhibit essentially the same level of effector function.

The skilled addressee will appreciate that greater effector function may be manifested in any of a number of ways, for example as a greater level of effect, a more sustained effect or a faster rate of effect.

For example, the anti-IL-3Rα immunoglobulin has or displays an effector function that includes antibody-dependent cell-mediated cytotoxicity (ADCC).

In one example, the Fc region comprises one or more amino acid modifications that increase its ability to induce enhanced effector function. In one example, the Fc region binds with greater affinity to one or more FcγRs. In one example, the Fc region has an affinity for an FcγR that is more than 1-fold greater than that of a wild-type Fc region or more than 5-fold greater than that of a wild-type Fc region or between 5-fold and 300-fold greater than that of a wild-type Fc region. In one example, the Fc region comprises at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the Fc region comprise at least one amino acid substitution selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y, numbered according to the EU index of Kabat. In one example, the Fc region comprises amino acid substitutions selected from the group consisting of V264I, F243L/V264I, L328M, I332E, L328M/I332E, V264I/I332E, S298A/I332E, S239E/I332E, S239Q/I332E, S239E, A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/ I332E, S239Q/V264I/I332E, S239EN264I/A330Y/I332E, S239D/A330Y/I332E, S239N/A330Y/I332E, S239D/ A330L/I332E, S239N/A330L/I332E, V264I/S298A/I332E, S239D/S298A/I332E, S239N/S298A/I332E, S239D/V264I/ I332E, S239D/V264I/S298A/I332E, S239D/V264I/A330L/ I332E, S239D/I332E/A330I, P230A, P230A/E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/A330Y/I332E/L235D, S239D/A330Y/I332E/V240I, S239D/A330Y/I332E/ V264T, S239D/A330Y/I332E/K326E, and S239D/A330Y/ I332E/K326T, numbered according to the EU index of Kabat.

In another example, the Fc region binds to FcγRIIIa more efficiently than to FcγRIIb. For example, the Fc region comprises at least one amino acid substitution at a position selected from the group consisting of: 234, 235, 239, 240, 264, 296, 330, and I332, numbered according to the EU index of Kabat. In one example, the Fc region comprises at least one amino acid substitution selected from the group consisting of: L234Y, L234I, L235I, S239D, S239E, S239N, S239Q, V240A, V240M, V264I, V264Y, Y296Q, A330L, A330Y, A330I, I332D, and I332E, numbered according to the EU index of Kabat. For example, the Fc region comprises amino acid substitutions selected from the group consisting of: I332E, V264I/I332E, S239E/I332E, S239Q/ I332E, Y296Q, A330L, A330Y, I332D, S239D, S239D/ I332E, A330Y/I332E, V264I/A330Y/I332E, A330L/I332E, V264I/A330L/I332E, L234Y, L234I, L235I, V240A, V240M, V264Y, A330I, S239D/A330L/I332E, S239D/ S298A/I332E, S239N/S298A/I332E, S239D/V264I/I332E, S239D/V264I/S298A/I332E, and S239D/V264I/A330L/ I332E, numbered according to the EU index of Kabat.

In a further example, the Fc region induces ADCC at a level greater than that mediated by a wild-type Fc region. For example, the Fc region induces ADCC at a level that is more than 5-fold or between 5-fold and 1000-fold greater than that induced by a wild-type Fc region. In one example, the Fc region comprise at least one amino acid substitution at a position selected from the group consisting of: 230, 233, 234, 235, 239, 240, 243, 264, 266, 272, 274, 275, 276, 278, 302, 318, 324, 325, 326, 328, 330, 332, and 335, numbered according to the EU index of Kabat. In one example, the Fc region comprises at least one amino acid substitutions selected from the group consisting of: P230A, E233D, L234E, L234Y, L234I, L235D, L235S, L235Y, L235I, S239D, S239E, S239N, S239Q, S239T, V240I, V240M, F243L, V264I, V264T, V264Y, V266I, E272Y, K274T, K274E, K274R, K274L, K274Y, F275W, N276L, Y278T, V302I, E318R, S324D, S324I, S324V, N325T, K326I, K326T, L328M, L328I, L328Q, L328D, L328V, L328T, A330Y, A330L, A330I, I332D, I332E, I332N, I332Q, T335D, T335R, and T335Y, numbered according to the EU index of Kabat. In one example, the Fc region comprises amino acid substitutions selected from the group consisting of: V264I, F243L/V264I, L328M, I332E, L328M/I332E, V264I/I332E, S298A/I332E, S239E/I332E, S239Q/I332E, S239E,A330Y, I332D, L328I/I332E, L328Q/I332E, V264T, V240I, V266I, S239D, S239D/I332D, S239D/I332E, S239D/I332N, S239D/I332Q, S239E/I332D, S239E/I332N, S239E/I332Q, S239N/I332D, S239N/I332E, S239Q/I332D, A330Y/I332E, V264I/A330Y/I332E, A330L/I332E, V264I/ A330L/I332E, L234E, L234Y, L234I, L235D, L235S, L235Y, L235I, S239T, V240M, V264Y, A330I, N325T, L328D/I332E, L328V/I332E, L328T/I332E, L328I/I332E, S239E/V264I/I332E, S239Q/V264I/I332E, S239E/V264I/ A330Y/I332E, S239D/A330Y/I332E, S239N/A330Y/ I332E, S239D/A330L/I332E, S239N/A330L/I332E, V264I/ S298A/I332E, S239D/S298A/I332E, S239N/S298A/I332E, S239D/V264I/I332E, S239D/V264I/S298A/I332E, S239D/ V264I/A330L/I332E, S239D/I332E/A330I, P230A, P230A/ E233D/I332E, E272Y, K274T, K274E, K274R, K274L, K274Y, F275W, N276L, Y278T, V302I, E318R, S324D, S324I, S324V, K326I, K326T, T335D, T335R, T335Y, V240I/V266I, S239D/A330Y/I332E/L234I, S239D/ A330Y/I332E/L235D, S239D/A330Y/I332E/V240I, S239D/A330Y/I332E/V264T, S239D/A330Y/I332E/ K326E, and S239D/A330Y/I332E/K326T, numbered according to the EU index of Kabat.

In one example, the Fc region comprises the following amino acid substitutions S239D/I332E, numbered according to the EU index of Kabat. This Fc region has about 14 fold increase in affinity for FcγRIIIa compared to a wild-type Fc region and about 3.3 increased ability to induce ADCC compared to a wild-type Fc region.

In one example, the Fc region comprises the following amino acid substitutions S239D/A330L/I332E, numbered according to the EU index of Kabat. This Fc region has about 138 fold increase in affinity for FcγRIIIa compared to a wild-type Fc region and about 323 increased ability to induce ADCC compared to a wild-type Fc region.

Additional amino acid substitutions that increase ability of a Fc region to induce effector function are known in the art and/or described, for example, in U.S. Pat. No. 6,737,056 or U.S. Pat. No. 7,317,091.

In one example, the glycosylation of the Fc region is altered to increase its ability to induce enhanced effector function. In this regard, native antibodies produced by mammalian cells typically comprise a branched, biantennary oligosaccharide that is generally attached by an N-linkage to Asn297 of the $C_H2$ domain of the Fc region. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some examples, Fc regions according to the present disclosure comprise a carbohydrate structure that lacks fucose attached (directly or indirectly) to an Fc region, i.e., the Fc region is "afucosylated". Such variants may have an improved ability to induce ADCC. Methods for producing afucosylated antibodies include, expressing the immunoglobulin in a cell line incapable of expressing α-1,6-fucosyltransferase (FUT8) (e.g., as described in Yumane-Ohnuki et al., *Biotechnol. Bioengineer.*, 87: 614-622, 2004), expressing the immunoglobulin in cells expressing a small interfering RNA against FUT8 (e.g., as described in Mori et al., *Biotechnol. Bioengineer.*, 88: 901-908, 2004), expressing the immunoglobulin in cells incapable of expressing guanosine diphosphate (GDP)-mannose 4,6-dehydratase (GMD) (e.g., as described in Kanda et al., *J. Biotechnol.*, 130: 300-310, 2007). The present disclosure also contemplates the use of immunoglobulins having a reduced level of fucosylation, e.g., produced using a cell line modified to express β-(1,4)-N-acetylglucosaminyltransferase III (GnT-III) (e.g., as described in Umana et al., *Nat. Biotechnol.*, 17: 176-180, 1999).

In one example, an immunoglobulin according to the present disclosure is afucosylated. For example, the immunoglobulin is produced in a cell (e.g., a mammalian cell, such as a CHO cell) that does not express FUT8.

Other methods include the use of cell lines which inherently produce antibodies capable of inducing enhanced Fc-mediated effector function (e.g. duck embryonic derived stem cells for the production of viral vaccines, WO2008/129058; Recombinant protein production in avian EBX® cells, WO 2008/142124).

Immunoglobulins useful in the methods of the present disclosure also include those with bisected oligosaccharides, e.g., in which a biantennary oligosaccharide attached to the Fc region is bisected by GlcNAc. Such immunoglobulins may have reduced fucosylation and/or improved ADCC function. Examples of such immunoglobulins are described, e.g., in U.S. Pat. No. 6,602,684 and US20050123546.

Immunoglobulins with at least one galactose residue in the oligosaccharide attached to the Fc region are also contemplated. Such immunoglobulins may have improved CDC function. Such immunoglobulins are described, e.g., in WO1997/30087 and WO1999/22764.

Non-limiting examples of immunoglobulins that display ADCC activity include the monoclonal antibodies designated herein as "hz7G3V1", "hz7G3V2" and "hz7G3V3". In each case the level of effector function exhibited by these immunoglobulins is enhanced relative to, or greater than that of, ch7G3 (a chimeric form of 7G3 comprising a wild-type human IgG1 Fc region) or hz7G3.

In another non-limiting example, an anti-IL-3Rα immunoglobulin may be produced de novo having enhanced effector function, such as enhanced ADCC function, as a result of binding a different epitope or having slower internalization kinetics (e.g. compared to ch7G3 or hz7G3).

Methods for determining the ability of an immunoglobulin to induce effector function and known in the art and/or described in more detail herein.

Additional Modifications

The present disclosure also contemplates additional modifications to an immunoglobulin.

For example, the immunoglobulin comprises one or more amino acid substitutions that increase the half-life of the immunoglobulin. For example, the immunoglobulin comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of an immunoglobulin, by reducing clearance from the blood.

Exemplary amino acid substitutions include T250Q and/or M428L according to the EU numbering system of Kabat. Additional or alternative amino acid substitutions are described, for example, in US20070135620.

Protein Production

In one example, an immunoglobulin described herein according to any example is produced by culturing a hybridoma under conditions sufficient to produce the immunoglobulin, e.g., as described herein and/or as is known in the art.

Recombinant Expression

In another example, an immunoglobulin described herein according to any example is recombinant.

In the case of a recombinant protein, nucleic acid encoding same can be cloned into expression vectors, which are then transfected into host cells, such as *E. coli* cells, yeast cells, insect cells, or mammalian cells, such as simian COS cells, Chinese Hamster Ovary (CHO) cells, human embryonic kidney (HEK) cells, or myeloma cells that do not otherwise produce immunoglobulin protein. Exemplary cells used for expressing an immunoglobulin are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art. See U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding an immunoglobulin (e.g., derived from the information provided herein), an enhancer element, a promoter, and a transcription termination sequence. The skilled artisan will be aware of suitable sequences for expression of an immunoglobulin. Exemplary signal sequences include prokaryotic secretion signals (e.g., pelB, alkaline phosphatase, penicillinase, Ipp, or heat-stable enterotoxin II), yeast secretion signals (e.g., invertase leader, a factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and

*S. pombe*, include, but are not limited to, the ADH1 promoter, the GAL1 promoter, the GAL4 promoter, the CUP1 promoter, the PHOS promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

The host cells used to produce the immunoglobulin may be cultured in a variety of media, depending on the cell type used. Commercially available media such as Ham's F10 (Sigma), Minimal Essential Medium ((MEM), (Sigma), RPM1-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for purifying an immunoglobulin are known in the art and/or described herein.

Where an immunoglobulin is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The immunoglobulin prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbour Laboratory, (1988).

The skilled artisan will also be aware that an immunoglobulin can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting immunoglobulin is then purified using methods known in the art, such as, affinity purification. For example, an immunoglobulin comprising a hexa-his tag is purified by contacting a sample comprising the immunoglobulin with nickel-nitrilotriacetic acid (Ni-NTA) that specifically binds a hexa-his tag immobilized on a solid or semi-solid support, washing the sample to remove unbound immunoglobulin, and subsequently eluting the bound immunoglobulin. Alternatively, or in addition a ligand or antibody that binds to a tag is used in an affinity purification method.

Assaying Activity of an Immunoglobulin

Determining Competitive Binding

Assays for determining an immunoglobulin that competitively inhibits binding of monoclonal antibody 7G3 will be apparent to the skilled artisan. For example, 7G3 is conjugated to a detectable label, e.g., a fluorescent label or a radioactive label. The labeled antibody and the test immunoglobulin are then mixed and contacted with IL-3Rα or an epitope thereof or a cell expressing same. The level of labeled 7G3 is then determined and compared to the level determined when the labeled antibody is contacted with the IL-3Rα, epitope or cells in the absence of the immunoglobulin. If the level of labeled 7G3 is reduced in the presence of the test immunoglobulin compared to the absence of the immunoglobulin, the immunoglobulin is considered to competitively inhibit binding of 7G3 to IL-3Rα.

Optionally, the test immunoglobulin is conjugated to different label to 7G3. This alternate labeling permits detection of the level of binding of the test immunoglobulin to IL-3Rα or the epitope or cell.

In another example, the immunoglobulin is permitted to bind to IL-3Rα prior to contacting the IL-3Rα with 7G3. A reduction in the amount of bound 7G3 in the presence of the immunoglobulin compared to in the absence of the immunoglobulin indicates that the immunoglobulin competitively inhibits 7G3 binding to IL-3Rα. A reciprocal assay can also be performed using labeled immunoglobulin and first allowing 7G3 to bind to IL-3Rα. In this case, a reduced amount of labeled immunoglobulin bound to IL-3Rα in the presence of 7G3 compared to in the absence of 7G3 indicates that the immunoglobulin competitively inhibits binding of 7G3 to IL-3Rα.

In another example, the epitope bound by the immunoglobulin is mapped to determine if it is the same or overlaps with the epitope bound by 7G3. Epitope mapping methods will be apparent to the skilled artisan. For example, a series of overlapping peptides spanning the IL-3Rα sequence, e.g., peptides comprising 10-15 amino acids are produced. The immunoglobulin is then contacted to each peptide and the peptide(s) to which it binds determined. This permits determination of peptide(s) comprising the epitope to which the immunoglobulin binds. If multiple non-contiguous peptides are bound by the immunoglobulin, the immunoglobulin may bind a conformational epitope.

Alternatively, or in addition, amino acid residues within IL-3Rα are mutated, e.g., by alanine scanning mutagenesis, and mutations that reduce or prevent immunoglobulin and/or 7G3 binding are determined. Any mutation that reduces or prevents binding of the immunoglobulin is likely to be within the epitope bound by the immunoglobulin.

Alternatively, or in addition, the immunoglobulin is produced using the epitope to which the 7G3 binds, and thus is likely to bind to the same epitope.

Optionally, the dissociation constant (Kd) of an immunoglobulin for IL-3Rα or an epitope thereof is determined. The "Kd" or "Kd value" for a IL-3Rα binding immunoglobulin is in one example measured by a radiolabeled IL-3Rα binding assay (RIA). This assay equilibrates the immunoglobulin with a minimal concentration of radioactive IL-3Rα in the presence of a titration series of unlabeled IL-3Rα. Following washing to remove unbound IL-3Rα, the amount of radioactivity is determined, which is indicative of the Kd of the protein.

According to another example the Kd or Kd value is measured by using surface plasmon resonance assays, e.g., using BIAcore surface plasmon resonance (BIAcore, Inc., Piscataway, N.J.) with immobilized IL-3Rα.

In some examples, proteins having a similar Kd or a higher Kd than 7G3 are selected, because they are likely to compete for binding to IL-3Rα.

Determining Neutralization

In some examples of the present disclosure, an immunoglobulin is capable of neutralizing IL-3 signaling.

Various assays are known in the art for assessing the ability of an immunoglobulin to neutralize signaling of a ligand through a receptor.

In one example, the immunoglobulin reduces or prevents IL-3 binding to the 3Rα chain and/or a heterodimer of IL-3Rα chain and IL-3Rβ chain. These assays can be performed as a competitive binding assay as described herein using labeled IL-3 and/or labeled immunoglobulin.

In another example, the immunoglobulin reduces or prevents IL-3-mediated histamine release from basophils. For example, low density leukocytes comprising basophils are incubated with IgE, IL-3 and various concentrations of the immunoglobulin. Control cells do not comprise immunoglobulin (positive control) or IL-3 (negative control). The level of released histamine is then assessed using a standard technique, e.g., RIA. An immunoglobulin that reduces the level of histamine release to a level less than the positive control is considered to neutralize IL-3 signaling. In one example, the level of reduction is correlated with immunoglobulin concentration. An exemplary method for assessing IL-3-mediated histamine release is described, for example, in Lopez et al., *J. Cell. Physiol.*, 145: 69, 1990.

In a further example, the immunoglobulin reduces or prevents IL-3-mediated proliferation of leukemic cell line TF-1. For example, TF-1 cells are cultured without IL-3 or GM-CSF for a time sufficient for them to stop proliferating (e.g., 24-48 hours). Cells are then cultured in the presence of IL-3 and various concentrations of the immunoglobulin. Control cells do not comprise immunoglobulin (positive control) or IL-3 (negative control). Cell proliferation is then assessed using a standard technique, e.g., 3H-thymidine incorporation. An immunoglobulin that reduces or prevents cell proliferation in the presence of IL-3 to a level less than the positive control is considered to neutralize IL-3 signaling.

Another assay for assessing IL-3 signaling neutralization comprises determining whether or not the immunoglobulin reduces or prevents IL-3-mediated effects on endothelial cells. For example, human umbilical vein endothelial cells (HUVECs) are cultured in the presence of IL-3 (optionally, with IFN-γ) and various concentrations of the immunoglobulin. The amount of secreted IL-6 is then assessed, e.g., using an enzyme linked immunosorbent assay (ELISA). Control cells do not comprise immunoglobulin (positive control) or IL-3 (negative control). An immunoglobulin that reduces or prevents IL-6 production in the presence of IL-3 to a level less than the positive control is considered to neutralize IL-3 signaling.

Other methods for assessing neutralization of IL-3 signaling are contemplated by the present disclosure.

Determining Effector Function

Methods for assessing ADCC activity are known in the art.

In one example, the level of ADCC activity is assessed using a $^{51}$Cr release assay, an europium release assay or a $^{35}$S release assay. In each of these assays, cells expressing IL-3Rα are cultured with one or more of the recited compounds for a time and under conditions sufficient for the compound to be taken up by the cell. In the case of a $^{35}$S release assay, cells expressing IL-3Rα can be cultured with $^{35}$S-labeled methionine and/or cysteine for a time sufficient for the labeled amino acids to be incorporated into newly synthesized proteins. Cells are then cultured in the presence or absence of the immunoglobulin and in the presence of immune effector cells, e.g., peripheral blood mononuclear cells (PBMC) and/or NK cells. The amount of $^{51}$Cr, europium and/or $^{35}$S in cell culture medium is then detected, and an increase in the presence of the immunoglobulin compared to in the absence of immunoglobulin indicates that the immunoglobulin has effector function. Exemplary publications disclosing assays for assessing the level of ADCC induced by an immunoglobulin include Hellstrom, et al. *Proc. Natl Acad. Sci. USA* 83:7059-7063, 1986 and Bruggemann, et al., *J. Exp. Med.* 166:1351-1361, 1987.

Other assays for assessing the level of ADCC induced by an immunoglobulin include ACTI™ nonradioactive cytotoxicity assay for flow cytometry (CellTechnology, Inc. CA, USA) or CytoTox 96® non-radioactive cytotoxicity assay (Promega, Wis., USA).

Alternatively, or additionally, effector function of an immunoglobulin is assessed by determining its affinity for one or more FcγRs, e.g., as described in U.S. Pat. No. 7,317,091.

C1q binding assays may also be carried out to confirm that the immunoglobulin is able to bind C1q and may induce CDC. To assess complement activation, a CDC assay may be performed (see, for example, Gazzano-Santoro et al, *J. Immunol. Methods* 202: 163, 1996.

Assessing Therapeutic Efficacy

In Vitro Assays

Various in vitro assays are available to assess the ability of an immunoglobulin to treat a disease or condition described herein, e.g., lupus.

For example, pDCs and/or basophils or cell populations comprising same (e.g., PBMC) are cultured in the presence or absence of an immunoglobulin and an inducer of those cells that occurs in a disease or condition (e.g., CpG oligonucleotides and/or immune complexes in the case of lupus). The efficacy of the immunoglobulin in treating the disease or condition is then assessed, e.g., by determining the level of IFNα secreted into cell culture medium using an ELISA. Alternatively or in addition the level of histamine secretion or IL-4, IL-6 and/or IL-13 secretion is assessed. A reduction in the level of any of these cytokines compared to in the absence of immunoglobulin (or in the presence of an isotype control immunoglobulin) indicates that the immunoglobulin is suitable for treating the disease or condition. Alternatively, or in addition, the level of cell death is assessed. An increase in cell death (particularly pDC and/or basophil cell death in the absence of a detectable increase in death of other cell types above background) is indicative of an immunoglobulin suitable for treating the disease or condition. In this regard, as discussed herein above, cytokines such as IFNα are considered to play a role in some diseases/conditions, e.g., lupus. Accordingly, an immunoglobulin that reduces IFNα production is considered to be suitable for treating such conditions.

In Vivo Assays

In one example, the efficacy of an immunoglobulin to treat a disease or condition is assessed using an in vivo assay.

For example, the immunoglobulin is administered to a non-human animal (e.g., a non-human primate) and the number/level of pDCs and/or basophils in circulation is assessed. An immunoglobulin that reduces the number/level of pDCs and/or basophils compared to prior to administration and/or in a control mammal to which the immunoglobulin has not been administered is considered suitable for treating the disease or condition.

In another example, the level of a cytokine, such as IFNα is detected in the circulation of a mammal, e.g., using an ELISA. An immunoglobulin that reduces the level of the cytokine compared to the level prior to administration and/or in a control mammal to which the immunoglobulin has not been administered is considered suitable for treating the disease or condition. Since cytokines such as IFNα are considered to play a role in some diseases/conditions, e.g., lupus, an immunoglobulin that reduces IFNα production is considered to be suitable for treating such conditions.

In another example, an immunoglobulin is administered to a non-human mammal (e.g., non-human primate) model of lupus. For example, plasma from humans suffering from SLE is infused into non-human primates, such as cynomolgus monkeys, for a time and under conditions sufficient to produce a model of SLE (e.g., as described in Pincus et al., Clin. Immunol., 105: 141-154, 2002). The immunoglobulin is administered to the non-human primates and its effect on SLE symptoms is assessed, e.g., using an assay described herein. For example, the level of anti-dsDNA antibodies and/or immune complexes is assessed. An immunoglobulin that reduces one or more SLE symptoms is considered suitable for treating SLE.

Conditions to be Treated

Diseases or conditions to be treated by the method of the present disclosure are typically associated with or are in part caused or mediated by type I interferons and/or are responsive to depletion, removal or at least partial elimination of dendritic cells that produce type I interferons and/or basophils. Suitably, the disease or condition is selected from systemic lupus erythematosus (SLE), Sjögrens syndrome and scleroderma including systemic scleroderma (SSc).

In one example, the disease or condition is lupus. For example, the disease or condition is discoid lupus, subacute cutaneous lupus erythematosus, drug-induced lupus, neonatal lupus, lupus nephritis or SLE.

A particular disease or condition is SLE.

In one example, the SLE is seronegative SLE, i.e., is not characterized by autoantibodies. Accordingly, in one example, a method of the present disclosure additionally comprises identifying a mammal suffering from seronegative SLE, e.g., by detecting the absence of autoantibodies such as those described herein.

In another example, the SLE is seropositive SLE. For example, the SLE is characterized by auto-antibodies such as, anti-nuclear antibodies (ANA), anti-C1q antibodies, anti-double-stranded DNA (dsDNA) antibodies, anti-Sm antibodies, anti-nuclear ribonucleoprotein antibodies, anti-phospholipid antibodies, anti-ribosomal P antibodies, anti-Ro/SS-A antibodies, anti-Ro antibodies, and anti-La antibodies. Accordingly, in one example, a method of the present disclosure additionally comprises identifying a mammal suffering from seropositive SLE, e.g., by detecting the presence of autoantibodies such as those described herein.

Methods for detecting autoantibodies will be apparent to the skilled artisan. For example, a serum or plasma sample from a subject is contacted with an antigen, e.g., dsDNA for a time and under conditions sufficient for an antibody-antigen complex to form. The resulting complexes are then contacted with a labeled antibody capable of binding to a mammalian antibody (e.g., an anti-Fc antibody) for a time and under conditions for a complex to form and the amount of label detected. Detection of the label indicates presence of the autoantibody.

The methods described herein according to any example may additionally comprise selecting a mammal for treatment on the basis of having a disease or condition or being at risk of developing a relapse of the disease or condition. Particular examples of such conditions and diseases are described above.

For example, an individual having lupus or at risk of developing lupus or a relapse thereof can be identified based on the detection of autoantibodies, e.g., as described above.

Diagnosis of SLE may additionally or alternatively be according to current American College of Rheumatology (ACR) criteria and/or active disease may be defined by one British Isles Lupus Activity Group's (BILAG) "A" criteria or two BILAG "B" criteria and/or by the European Consensus Lupus Activity Measure (ECLAM) and/or by the Lupus Activity Index (LAI) and/or by the National Institutes of Health SLE Index Score (SIS) and/or by the Systemic Lupus Activity Measure (SLAM) and/or by the SLE disease activity index (SLEDAI). Some signs, symptoms, or other indicators used to diagnose SLE adapted from Tan et al. Arth Rheum 25, 1982 may be malar rash such as rash over the cheeks, discoid rash, or red raised patches, photosensitivity such as reaction to sunlight, resulting in the development of or increase in skin rash, oral ulcers such as ulcers in the nose or mouth, arthritis, such as non-erosive arthritis involving two or more peripheral joints (arthritis in which the bones around the joints do not become destroyed), serositis, pleuritis or pericarditis, renal disorder such as excessive protein in the urine (greater than 0.5 gm/day or $3^+$ on test sticks) and/or cellular casts (abnormal elements derived from the urine and/or white cells and/or kidney tubule cells), neurologic signs, symptoms, or other indicators, seizures (convulsions), and/or psychosis in the absence of drugs or metabolic disturbances that are known to cause such effects, and hematologic signs, symptoms, or other indicators such as hemolytic anemia or leukopenia (white bloodcount below 4,000 cells per cubic millimeter) or lymphopenia (less than 1,500 lymphocytes per cubic millimeter) or thrombocytopenia (less than 100,000 platelets per cubic millimeter). The leukopenia and lymphopenia must be detected on two or more occasions. The thrombocytopenia must be detected in the absence of drugs known to induce it. The present disclosure is not limited to these signs, symptoms, or other indicators of lupus.

In one example, the mammal has been diagnosed as suffering from severe SLE, e.g., by one or more of the foregoing measures.

A mammal at risk of suffering from a relapse of lupus may also display one or more of the foregoing symptoms and has previously suffered from symptoms of lupus. Alternatively or additionally, a mammal at risk of suffering from a relapse of lupus is known to have previous suffered from lupus and is being treated with estrogen therapy and/or a sulphonamide drug and/or an interferon.

In one example, the subject suffers from Sjörgen's syndrome. Each example described herein shall be taken to apply mutatis mutandis to the treatment of Sjörgen's syndrome.

Sjörgen's syndrome can be diagnosed (or a subject suffering from Sjörgen's syndrome can be selected) by detecting autoantibodies (e.g., antinuclear antibodies (e.g., SSA/Ro and SSB/La), rheumatoid factor, alpha-Fodrin and/or anti-thyroid antibodies), dryness of the eyes, salivary gland inflammation and/or anemia.

In one example, the Sjörgen's syndrome is associated with lupus, i.e., occurs in a subject suffering from lupus.

In one example, the subject suffers from scleroderma. Each example described herein shall be taken to apply mutatis mutandis to the treatment of scleroderma.

In one example, the scleroderma is systemic scleroderma, such as limited systemic scleroderma or diffuse systemic scleroderma.

Scleroderma can be diagnosed (or a subject suffering from scleroderma can be selected) by detecting autoantibodies (e.g., anti-topoisomerase antibodies (in a diffuse systemic form of scleroderma), anti-centromere antibodies (in a limited systemic form of scleroderma), anti-U3 antibodies or anti-RNA polymerase antibodies), local or widespread signs of inflammation of the skin (redness, swelling, tenderness, itching, and pain) that can lead to skin tightness or hardening of the skin, particularly on the fingers, feet, face, and neck. Various symptoms can also occur in, e.g., the digestive system, lungs and blood vessels.

In one example, the scleroderma is associated with lupus, i.e., occurs in a subject suffering from lupus.

In one example, the mammal is resistant to, does not adequately respond to, or is unsuitable for treatment with another compound used to treat the disease or condition. For example, the mammal is resistant to, does not adequately respond to, or is unsuitable for treatment with a corticosteroid and/or an immunosuppressant and/or an antimalarial agent and/or azathioprine and/or cyclophosphamide and/or mycophenolate mofetil and/or methotrexate and/or an anti-TNF antibody and/or an anti-CD20 antibody and/or an anti-IL6 antibody and/or an anti-CD22 antibody.

Compositions

Suitably, in compositions or methods for administration of the anti-IL-3Rα immunoglobulin to a mammal, the immunoglobulin is combined with a pharmaceutically acceptable carrier, diluent and/or excipient, as is understood in the art. Accordingly, one example of the present disclosure provides a pharmaceutical composition comprising the anti-IL.3Rα immunoglobulin combined with a pharmaceutically acceptable carrier, diluent and/or excipient. In another example, the disclosure provides a kit comprising a pharmaceutically acceptable carrier, diluent and/or excipient suitable for combining or mixing with the immunoglobulin prior to administration to the mammal. In this example, the kit may further comprise instructions for use.

In general terms, by "carrier, diluent or excipient" is meant a solid or liquid filler, binder, diluent, encapsulating substance, emulsifier, wetting agent, solvent, suspending agent, coating or lubricant that may be safely administered to any mammal, e.g., a human. Depending upon the particular route of administration, a variety of acceptable carriers, diluents or excipients, known in the art may be used, as for example described in Remington's Pharmaceutical Sciences (Mack Publishing Co. N.J. USA, 1991).

By way of example only, the carriers, diluents or excipients may be selected from a group including sugars (e.g. sucrose, maltose, trehalose, glucose), starches, cellulose and its derivatives, malt, gelatine, talc, calcium sulphate, oils inclusive of vegetable oils, synthetic oils and synthetic mono- or di-glycerides, lower alcohols, polyols, alginic acid, phosphate buffered solutions, lubricants such as sodium or magnesium stearate, isotonic saline and pyrogen-free water. For example, the carrier, diluent or excipient is compatible with, or suitable for, parenteral administration. Parenteral administration includes any route of administration that is not through the alimentary canal. Non-limiting examples of parenteral administration include injection, infusion and the like. By way of example, administration by injection includes intravenous, intra-arterial, intramuscular and subcutaneous injection. Also contemplated is delivery by a depot or slow-release formulation which may be delivered intradermally, intramuscularly and subcutaneously, for example.

Combination Therapies

In one example, the immunoglobulin that binds to IL-3Rα is administered in combination with another compound useful for treating a disease or condition, e.g., lupus (such as SLE), either as combined or additional treatment steps or as additional components of a therapeutic formulation.

For example, the other compound is an anti-inflammatory compound. Alternatively, or additionally, the other compound is an immunosuppressant. Alternatively, or additionally, the other compound is a corticosteroid, such as prednisone and/or prednisolone. Alternatively, or additionally, the other compound is an antimalarial compound, such as hydroxychloroquine or chloroquinine. Alternatively, or additionally, the other compound is methotrexate. Alternatively, or additionally, the other compound is azathioprine. Alternatively, or additionally, the other compound is cyclophosphamide. Alternatively, or additionally, the other compound is mycophenolate mofetil. Alternatively, or additionally, the other compound is an anti-CD20 antibody (e.g., rituximab or ofatumumab). Alternatively, or additionally, the other compound is an anti-CD22 antibody (e.g., epratuzumab). Alternatively, or additionally, the other compound is an anti-TNF antibody (e.g., infliximab or adalimumab or golimumab). Alternatively, or additionally, the other compound is a CTLA-4 antagonist (e.g., abatacept, CTLA4-Ig). Alternatively, or additionally, the other compound is an anti-IL-6 antibody. Alternatively, or additionally, the other compound is a BLys antagonist, such as an anti-BLys antibody (e.g., belimumab).

Dosages and Timing of Administration

For the prevention or treatment of a disease or condition or relapse thereof, the appropriate dosage of an active agent (i.e., an anti-IL-3Rα immunoglobulin), will depend on the type of disease to be treated, the severity and course of the disease, whether the immunoglobulin is administered for preventive or therapeutic purposes, previous therapy, the patient's clinical history and response to the immunoglobulin, and the discretion of the attending physician. The particular dosage regimen, i.e., dose, timing, and repetition, will depend on the particular individual and that individual's medical history as assessed by a physician. Typically, a clinician will administer an immunoglobulin until a dosage is reached that achieves the desired result.

Methods of the present disclosure are useful for treating, ameliorating or preventing the symptoms of diseases or conditions, such as lupus (e.g., SLE) in a mammal, or for improving the prognosis of a mammal. The quality of life in a mammal suffering from lupus may be improved, and the symptoms of lupus may be reduced or eliminated following treatment with the immunoglobulin. Methods of the present disclosure are also useful for delaying development of or preventing lupus in an individual at risk of developing lupus or a relapse thereof.

For in vivo administration of the immunoglobulins described herein, normal dosage amounts may vary from about 10 ng/kg up to about 100 mg/kg of an individual's body weight or more per day. Exemplary dosages and ranges thereof are described herein. For repeated administrations over several days or longer, depending on the severity of the disease or disorder to be treated, the treatment can be sustained until a desired suppression of symptoms is achieved.

In some examples, the immunoglobulin is administered at an initial (or loading) dose of between about 1 mg/kg to about 30 mg/kg, such as from about 1 mg/kg to about 10 mg/kg, or about 2 mg/kg or about 3 mg/kg or 4 mg/kg or 5 mg/kg. The immunoglobulin can then be administered at a maintenance dose of between about 0.0001 mg/kg to about 1 mg/kg, such as from about 0.0005 mg/kg to about 1 mg/kg, for example, from about 0.001 mg/kg to about 1 mg/kg, such as about 0.005 mg/kg to about 1 mg/kg, for example from about 0.1 mg/kg to about 1 mg/kg, such as about 0.2 mg/kg or 0.3 mg/kg or 0.4 mg/kg or 0.5 mg/kg. The maintenance doses may be administered every 7-30 days, such as, every 10-15 days, for example, every 10 or 11 or 12 or 13 or 14 or 15 days.

In some examples, the immunoglobulin is administered at a dose of between about 0.0001 mg/kg to about 50 mg/kg, such as between about 0.0005 mg/kg to about 50 mg/kg, for example, between about 0.001 mg/kg to about 45 mg/kg, for example, between about 0.005 mg/kg to about 40 mg/kg, such as between about 0.05 mg/kg to about 35 mg/kg. For example, the immunoglobulin is administered at a dose of between about 0.01 mg/kg to about 1 mg/kg, such as from about 0.1 mg/kg to about 1 mg/kg, such as about 0.2 mg/kg or 0.3 mg/kg or 0.4 mg/kg or 0.5 mg/kg (e.g., without a higher loading dose). In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the immunoglobulin is administered every 7 days or every 14 days or every 21 days.

In some examples, the immunoglobulin is administered at a dose of between about 1 mg/kg to about 30 mg/kg, such as from about 1 mg/kg to about 10 mg/kg, or about 2 mg/kg or about 3 mg/kg or 4 mg/kg or 5 mg/kg, or such as from about 10 mg/kg to 30 mg/kg, such as about 10 mg/kg or 15 mg/kg or 20 mg/kg or 25 mg/kg (e.g., without a lower maintenance dose). In some examples, numerous doses are administered, e.g., every 10-70 days, such as every 14-70 days, such as, every 14-60 days, for example, every 14-50 days, such as every 14-40 days, or every 14-30 days. For example the doses are administered every 14 or 21 or 25 or 28 or 35 or 40 or 42 or 49 or 50 or 55 or 57 or 63 or 70 days. For example, the immunoglobulin is administered every 21 days or every 28 days or every 35 days or every 42 days or every 49 days or every 56 days.

In some examples, at the time of commencing therapy, the mammal is administered the immunoglobulin on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Dosages for a particular immunoglobulin may be determined empirically in mammals who have been given one or more administrations of the immunoglobulin. To assess efficacy of an immunoglobulin, a clinical symptom of a disease or condition, e.g., lupus (such as SLE) can be monitored.

Administration of an immunoglobulin according to the methods of the present disclosure can be continuous or intermittent, depending, for example, on the recipient's physiological condition, whether the purpose of the administration is therapeutic or prophylactic, and other factors known to skilled practitioners. The administration of an immunoglobulin may be essentially continuous over a preselected period of time or may be in a series of spaced doses, e.g., either during or after development of lupus (such as SLE).

In one example, the immunoglobulin is administered so as to achieve a reduction in a score assessing the severity of SLE, e.g., BILAG criteria and/or ECLAM and/or LAI and/or SIS and/or SLAM and/or SLEDAI. For example, treatment with the immunoglobulin achieves a reduction in one or two or three points according to the BILAG and/or SLEDAI. For example, the reduction is achieved by 15 weeks after commencing therapy or by 30 weeks after commencing therapy or by 52 weeks after commencing therapy. For example, the effect is maintained for about 20 weeks or 30 weeks or 40 weeks or 50 weeks after commencing therapy.

NON-LIMITING EXAMPLES

The antibody designations used in the Examples are as follows: (i) an anti-IL-3Rα mouse monoclonal antibody (designated 7G3); (ii) a chimeric version of 7G3 with a human IgG1 constant domain (designated ch7G3); (iii) a humanized IgG1 version of 7G3 (designated hz7G3); (iv) a humanized version of 7G3 containing Xencor V90, S239D/I332E, G1/G2 Fc modifications (designated hz7G3V1); (v) a humanized version of 7G3 containing Xencor V209, S239D/I332E/A330L G1/G2 Fc modifications (designated hz7G3V2); and (vi) an afucosylated version of hz7G3 produced using a fucosyltransferase deficient CHO cell line (designated hz7G3V3).

Example 1

Expression of IL-3Rα

PBMC were identified from humans using standard techniques and various cell lineages isolated using antibodies that bind to lineage specific cell surface markers. Using Quantibrite™ beads (BD Biosciences) the number of IL-3Rα molecules per cell was determined for each lineage. As shown in FIG. 1, IL-3Rα is expressed highly on pDCs and basophils and at low levels on other cell lineages tested. This limited expression pattern makes IL-3Rα a useful target for an antibody designed to selectively eliminate pDCs and basophils.

Example 2

Anti-IL-3Rα mAb Depletion of Human pDCs In Vitro

Peripheral blood mononuclear cells (PBMC) were isolated from a normal donor by Ficoll™ separation and incubated at 37° C. for various times in RPMI/10% FCS without antibody (no antibody), with 10 µg/ml anti-ch7G3 or with 10 µg/ml antihz7G3V3. $1 \times 10^6$ cells were routinely cultured in a 200 µL volume in a 96 well U-bottom plate. Analysis of plasmacytoid dendritic cell (pDCs) numbers and basophil numbers was determined by flow cytometry (Tables 1 and 2, respectively). Human pDCs were identified by flow cytometry as being lineage marker negative (CD20−, CD3−, CD14−, CD19− CD56−), HLA-DR positive, CD11c negative and IL-3Rα positive (see gated box in flow diagrams). Human basophils were identified by flow cytometry as being lineage marker negative (CD20−, CD3−, CD14−, CD19− CD56−), IgE positive and IL-3Rα positive. The anti-IL-3Rα antibody containing modifications in the Fc-domain (hz7G3V3) depleted pDCs and basophils from PBMC as early as 4 h post addition and maintained pDC and basophil depletion up to 48 h post addition. Addition of an anti-IL-3R antibody without enhanced effector function (ch7G3) resulted in reduced pDC numbers observed at 24 h and 48 h post addition. However the observed effect was substantially less than that observed for hz7G3V3 and did not substantially fully deplete pDCs by 48 hours.

TABLE 1

Percentage of pDCs in cell culture following antibody treatment.

| | pDCs (% of total cells remaining in culture) | | |
|---|---|---|---|
| | 4 h | 24 h | 48 h |
| Control (no antibody) | 0.14 | 0.05 | 0.07 |
| ch7G3 | 0.1 | 0.02 | 0.005 |
| hz7G3V3 | 0.008 | 0 | 0 |

TABLE 2

Percentage of basophils in cell culture following antibody treatment.

| | Basophils (% of total cells remaining in culture) | | |
|---|---|---|---|
| | 4 h | 24 h | 48 h |
| Control (no antibody) | 0.66 | 1.08 | 1.94 |
| hz7G3V3 | 0.25 | 0.07 | 0 |

Example 3

In Vivo Anti-IL-3Rα Depletion of pDCs and Basophils in Non-Human Primates

A non-GLP cynomolgous non-human primate (NHP) study was conducted at the Australian National Primate Facility in accordance with their standard operating procedures. All protocols and amendments were approved by the Institutional Animal Care and Use Committee. Naive monkeys were administered a single dose of neutralizing anti-IL-3Rα antibodies with modifications in the Fc-domain that enhanced antibody effector function (hz7G3V3) via intravenous infusion. Peripheral blood was collected at various time points and analysis of NHP basophils and pDCs perfumed by flow cytometry. NHP basophils were identified by flow cytometry as being IgE+/CD123 positive. pDCs were identified by flow cytometry as being lineage marker negative (CD20$^-$, CD3$^-$, CD14$^-$, CD19$^-$, CD56$^-$), HLA-DR positive, CD11c negative and IL-3Rα positive.

Figure 2:
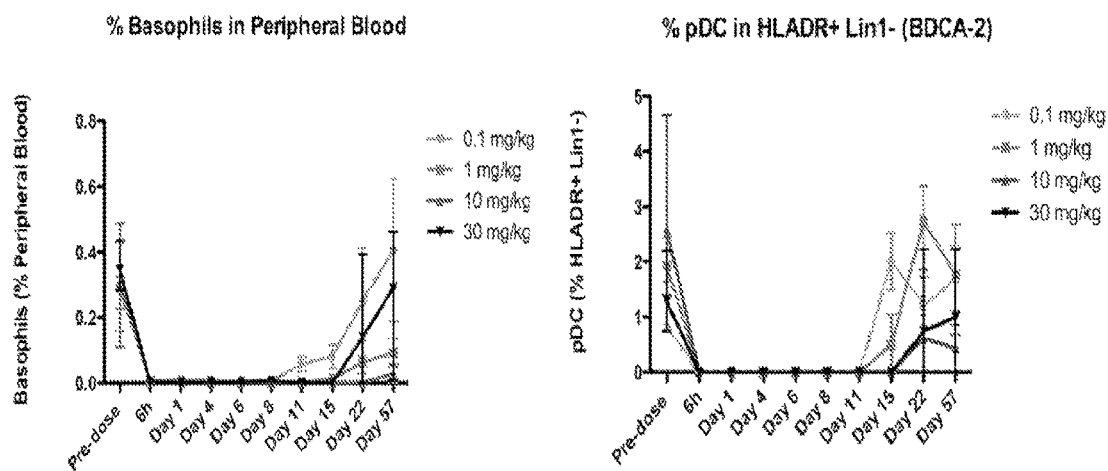
FIG. 2 includes two graphical representations showing the percentage of basophils (left hand side) or pDCs (right hand side) before and after administration of various dosages of an afucosylated humanized antibody that binds IL-3Rα (hz7G3V3). Numbers are represented as a percentage of total cells in a peripheral blood sample (Y-axis). The time of collection of peripheral blood relative to the time of administration of the antibody is indicated on the X-axis. The dosage of antibody is also indicated.

Administration of hz7G3V3 resulted in considerable reduction in the number of basophils and pDCs in the peripheral blood at all doses, evident as early as 6 hours post antibody administration. This reduction was sustained for over 8 days before the dose-dependent return of both cell types at either day 11 (basophils) or day 15 (pDCs) (FIG. 2).

No significant reduction in any other cell type tested (including neutrophils, T cells, B cells, monocytes and red blood cells) was observed for any monkey at any dose and no adverse events were observed. These data indicate that hz7G3V3 selectively depletes pDCs and basophils when administered in vivo and that pDC and basophil populations can recover when hz7G3V3 is eliminated from the system.

Example 4

In Vitro Comparison of ADCC Activity of Anti-IL-3Rα mAbs

Human pDCs and NK cells were isolated from two healthy buffy coats using negative selection kits as detailed by the manufacturer (Miltenyi Biotech). NK cells (effectors "E"=100,000 cells) and pDCs (targets "T"=10,000 cells), were incubated together in the presence of 10 µg/ml, of various versions of an anti-IL-3Rα antibody (hz7G3V1, hz7G3V2 and hz7G3V3) at a E:T ratio of 10:1 in a final volume of 150 µL in 96 well U-bottom plates. Autologous lysis (pDC1-NK1, pDC2-NK2) and allogeneic lysis (pDC1-NK2, pDC2-NK1) were examined following 4 hours incubation at 37° C. in RPMI/10% FCS. Cell lysis was measured using a LDH CytoTox 96 Non-Radioactive Cytotoxicity kit (Promega).

Specific Lysis was determined by the following calculation:

Specific Lysis=[Sample Lysis−Spontaneous Lysis]/ [Maximal Lysis Spontaneous Lysis]×100%.

Maximal Lysis was evaluated by addition of Extran™ to a final concentration of 0.75% (v/v). Spontaneous Lysis was that which occurred in wells with cells alone (no Ab).

Figure 3:
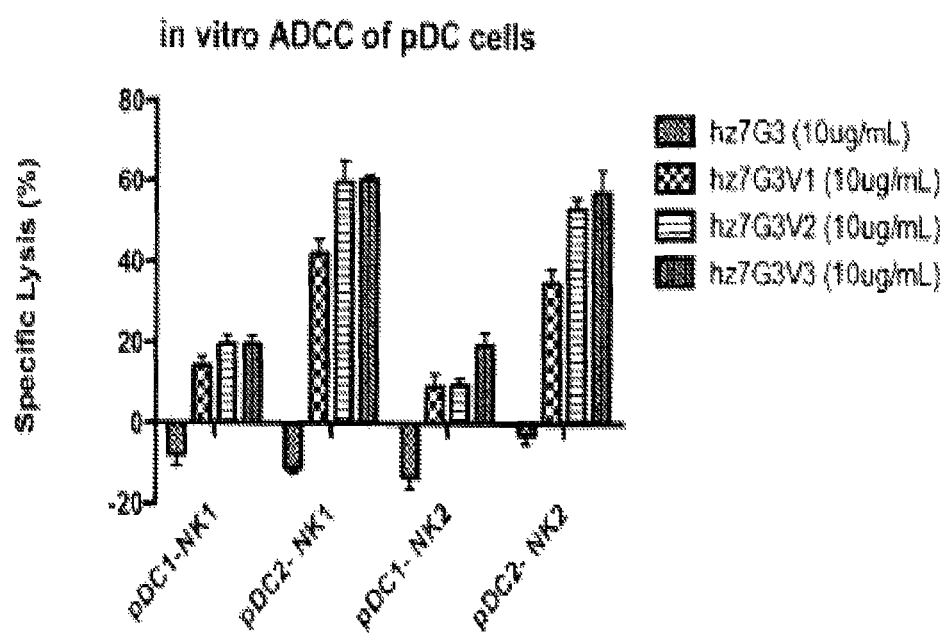
FIG. 3 is a graphical representation showing the level of cell lysis caused by ADCC induced by various antibodies under different conditions. The nomenclature designating the antibodies studied is consistent with the description herein. Antibodies were studied under autologous target-effector conditions (pDC1-NK1, pDC2-NK2) and allogeneic target-effector conditions (pDC1-NK2, pDC2-NK1). Results are presented as a percentage of specific lysis as determined as a function of spontaneous lysis and maximal lysis achieved with Extran™.

Significant levels of pDC lysis were observed with anti-IL-3Rα mAbs that had been engineered for enhanced ADCC capacity compared to the anti-IL-3Rα antibody hz7G3 (FIG. 3).

Example 5

Inhibition of Interferon Production by Anti-IL-3Rα mAbs

Figure 4:
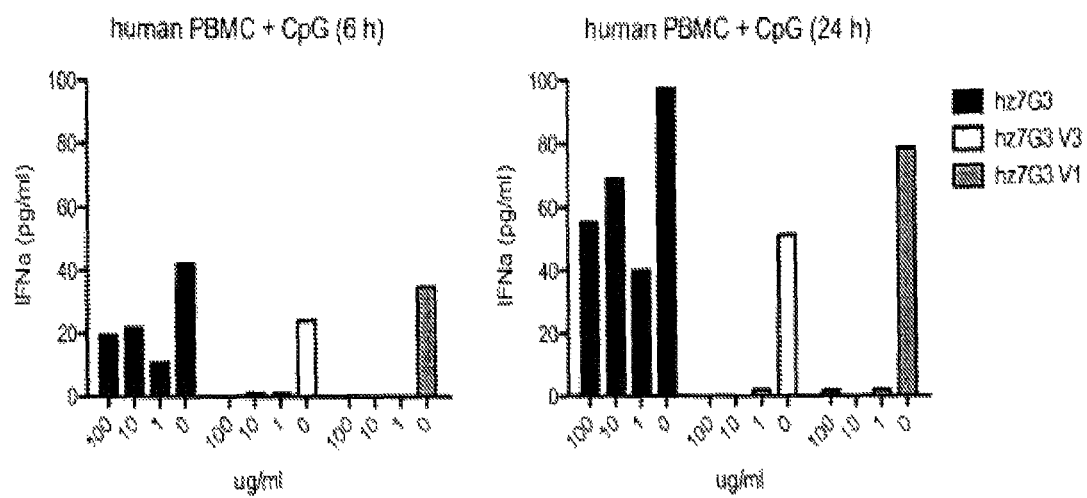
FIG. 4 includes two graphical representations showing the amount of IFNα secreted into cell culture medium by PBMC containing pDCs activated with a type C CpG oligonucleotide. Cells were cultured with the indicated antibody at the concentration indicated on the X-axis. The amount of IFNα detected using an ELISA is indicated on the Y-axis. Results of assays performed 6 hours (left hand side) and 24 hours (right hand side) after activation with the oligonucleotide are shown.

Peripheral blood mononuclear cells (PBMC) were isolated from a normal donor and incubated at 37° C. for 18 h without antibody (0 µg/ml), with increasing doses (1, 10 or 100 µg/ml) of the anti-IL-3R antibody hz7G3 or anti-IL-3R antibodies containing modifications in the Fc-domain that enhanced antibody effector function (hz7G3V3 and hz7G3V1). Type C CpG oligonucleotide (5 µM) was added to activate plasmacytoid dendritic cells. Supernatants were collected at either 6 h or 24 h post activation and were assayed for IFNα production by ELISA. As shown in FIG. 4, addition of the antibody hz7G3 resulted in a small reduction in IFNα production, and this effect did not appear to be affected by increased dose of antibody. In contrast, the addition of anti-IL-3R antibodies containing modifications in the Fc-domain (hz7G3V3 and hz7G3V1) considerably reduced IFNα production from PBMC at both 6 h and 24 h post activation at all doses of antibody.

Figure 5:
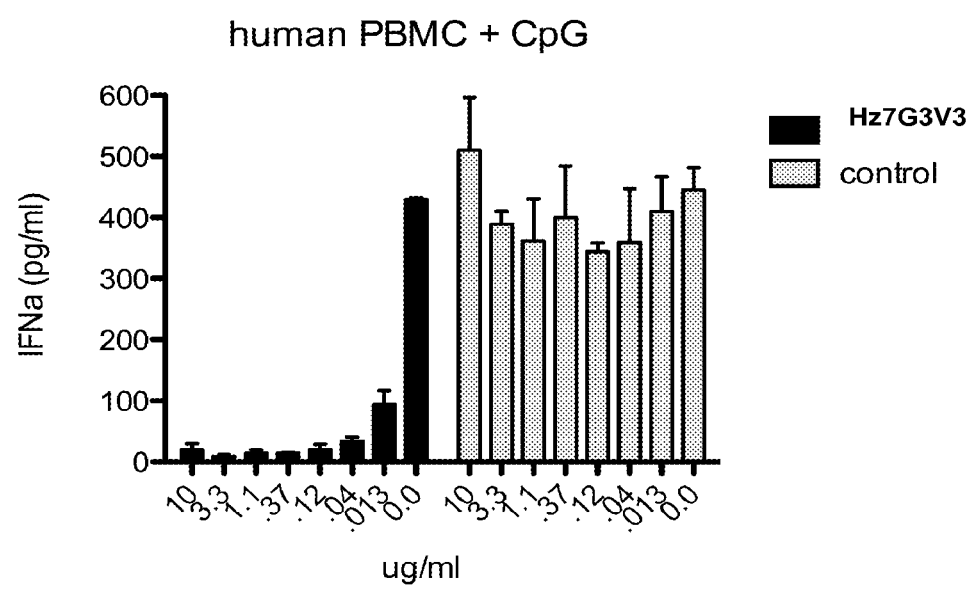
FIG. 5 is a graphical representation showing the amount of IFNα secreted into cell culture medium by PBMC containing pDCs activated with a type C CpG oligonucleotide. Cells were cultured with various concentrations of an afucosylated humanized antibody that binds IL-3Rα (hz7G3V3) or an isotype control antibody (as indicated). The amount of IFNα detected using an ELISA is indicated on the Y-axis. Results of assays performed 24 hours after activation with the oligonucleotide are shown.

In a further study, PBMC were isolated from a normal donor and incubated at 37° C. for 18 h without antibody or with increasing doses of hz7G3V3 or isotype control antibodies. Type C CpG oligonucleotide (5 µM) was added to activate pDCs. Supernatants were collected at 24 h post activation and were assayed for IFNγ production by ELISA. Addition of hz7G3V3 considerably reduced IFNα production from PBMC. The in vitro depletion of pDCs by hz7G3V3 correlates with inhibition of IFNα production from PBMC treated with the TLR-7/9 ligand, CpG (FIG. 5). The addition of CpG to PBMC induces IFNα production in a similar manner to SLE immune complexes, which contain chromatin components that are predominantly TLR-7/9 agonists. These data indicate that hz7G3V3 can effectively eliminate the source of IFNα induced by TLR-7/9 agonists in peripheral blood cells. The data also indicate that other cell types in peripheral blood that are not targeted by hz7G3V3 cannot compensate for the loss of pDCs for IFNα production in response to TLR-7/9 stimulation.

Figure 6:
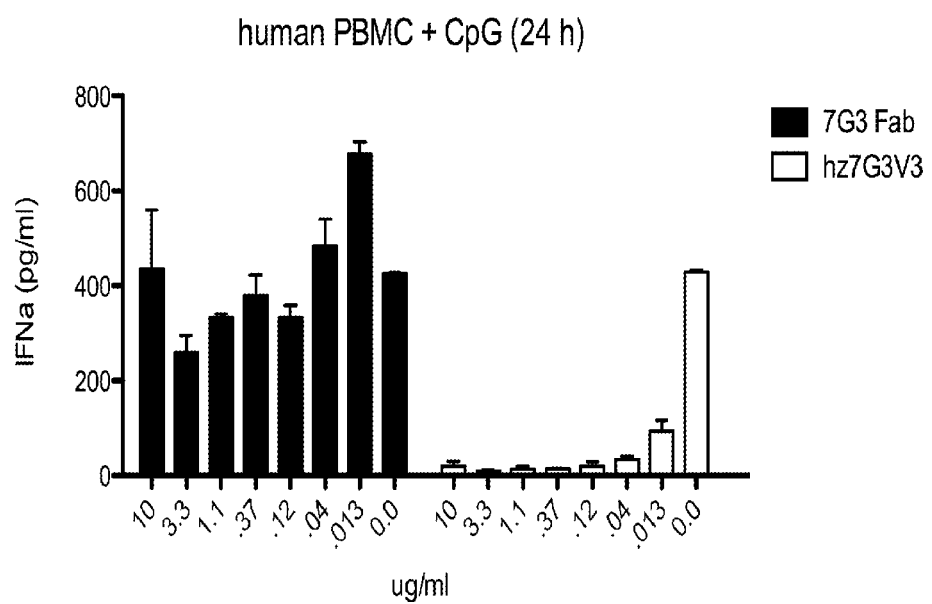
FIG. 6 is a graphical representation showing the amount of IFNα secreted into cell culture medium by PBMC containing pDCs activated with a type C CpG oligonucleotide. Cells were cultured with various concentrations of an afucosylated humanized antibody that binds IL-3Rα (hz7G3V3) or a Fab fragment of the same antibody (7G3 Fab) (as indicated). The amount of IFNα detected using an ELISA is indicated on the Y-axis. Results of assays performed 24 hours after activation with the oligonucleotide are shown.

A further study was performed to determine the effect of cell depletion on IFNα levels. PBMC were isolated from a normal donor and incubated at 37° C. for 18 h without antibody (0 μg/ml), with increasing doses of a neutralizing anti-IL-3R antibodies containing modifications in the Fc-domain that enhanced antibody effector function (hz7G3V3) or the Fab region of the same antibody (hz7G3 Fab). Type C CpG oligonucleotide (5 μM) was added to activate pDCs. Supernatants were collected at either 6 h or 24 h post activation and were assayed for IFNα production by ELISA. As shown in FIG. 6, addition of neutralizing anti-IL-3R Fab (hz7G3 Fab) that lacks effector function did not reduce IFNα production, while addition of anti-IL-3R antibodies containing modifications in the Fc-domain (hz7G3V3) completely inhibited IFNα production from PBMC at both 6 h and 24 h post activation.

The disclosure of each patent and scientific document, computer program and algorithm referred to in this specification is incorporated by reference in its entirety.

The invention claimed is:

1. A method of treating lupus in a mammal, the method comprising administering to the mammal an antibody which binds an interleukin 3 receptor α (IL-3Rα) chain and which kills a plasmacytoid dendritic cell (pDC) or basophil to which it binds to thereby treat lupus in the mammal, wherein the antibody comprises the variable regions of antibody 7G3 or is a humanized form of antibody 7G3, and wherein the antibody is not conjugated to a toxic compound that kills a cell to which the antibody binds, and wherein the antibody is capable of inducing an enhanced level of effector function, and wherein the effector function is antibody-dependent cell cytotoxicity (ADCC) and/or antibody-dependent cell mediated phagocytosis (ADCP).

2. The method of claim 1, wherein the lupus is systemic lupus erythematosus (SLE).

3. The method of claim 1, wherein the IL-3Rα chain is expressed by a pDC that produces one or more type I interferons and/or wherein the IL-3Rα chain is expressed by a basophil that produces one or more cytokines.

4. The method of claim 1, wherein the antibody neutralizes IL-3 signaling.

5. The method of claim 1, wherein the antibody is a chimeric antibody.

6. The method of claim 1, wherein the antibody is a humanized antibody.

7. The method of claim 1, wherein the humanized antibody comprises a light chain variable region ($V_L$) comprising the sequence set forth in SEQ ID NO: 3 and a heavy chain variable region ($V_H$) comprising the sequence set forth in SEQ ID NO: 2.

8. The method of claim 1, wherein the antibody comprises a Fc region that is afucosylated.

9. The method of claim 1, wherein the antibody comprises a human Fc portion comprising one or more amino acid sequence substitutions that enhance the effector function induced by the antibody.

10. The method of claim 9, wherein the one or more amino acid sequence substitutions in the human Fc portion are:
    (i) S239D, A330L and I332E according to the EU numbering system of Kabat; or
    (ii) S239D and I332E according to the EU numbering system of Kabat.

11. The method of claim 10, wherein the antibody comprises a light chain comprising the sequence set forth in SEQ ID NO: 5 and a heavy chain comprising the sequence set forth in SEQ ID NO: 7 (hz7G3V2).

12. The method of claim 1, wherein following administration of the antibody the number of plasmacytoid dendritic cells (pDCs) and basophils in circulation in the mammal is reduced by at least about 50% compared to the number of the pDCs and/or basophils in circulation in the mammal prior to administering the antibody.

13. The method of claim 12, wherein at least about six hours following administration of the antibody, the number of pDCs and basophils in circulation in the mammal is reduced by at least about 50% compared to the number of the pDCs and/or basophils in circulation in the mammal prior to administering the antibody.

14. The method of claim 12, wherein the number of pDCs and basophils in circulation in the mammal is reduced by at least about 50% compared to the number of pDCs and/or basophils in circulation in the mammal prior to administering the antibody for at least 7 days post administration without further administrations of the antibody.

15. The method of claim 1 comprising administering between about 0.001 mg/kg and 50 mg/kg of antibody to the mammal.

16. The method of claim 15, wherein the antibody is administered to the mammal a plurality of times and wherein the period between administrations is at least about 11 days.

* * * * *

SEQUENCE LISTING

```
<160> NUMBER OF SEQ ID NOS: 7

<210> SEQ ID NO 1
<211> LENGTH: 359
<212> TYPE: PRT
<213> ORGANISM: Homo sapiens

<400> SEQUENCE: 1

Lys Glu Asp Pro Asn Pro Pro Ile Thr Asn Leu Arg Met Lys Ala Lys
1               5                   10                  15

Ala Gln Gln Leu Thr Trp Asp Leu Asn Arg Asn Val Thr Asp Ile Glu
            20                  25                  30

Cys Val Lys Asp Ala Asp Tyr Ser Met Pro Ala Val Asn Asn Ser Tyr
        35                  40                  45

Cys Gln Phe Gly Ala Ile Ser Leu Cys Glu Val Thr Asn Tyr Thr Val
    50                  55                  60

Arg Val Ala Asn Pro Pro Phe Ser Thr Trp Ile Leu Phe Pro Glu Asn
65                  70                  75                  80

Ser Gly Lys Pro Trp Ala Gly Ala Glu Asn Leu Thr Cys Trp Ile His
                85                  90                  95

Asp Val Asp Phe Leu Ser Cys Ser Trp Ala Val Gly Pro Gly Ala Pro
            100                 105                 110

Ala Asp Val Gln Tyr Asp Leu Tyr Leu Asn Val Ala Asn Arg Arg Gln
        115                 120                 125

Gln Tyr Glu Cys Leu His Tyr Lys Thr Asp Ala Gln Gly Thr Arg Ile
    130                 135                 140

Gly Cys Arg Phe Asp Asp Ile Ser Arg Leu Ser Ser Gly Ser Gln Ser
145                 150                 155                 160

Ser His Ile Leu Val Arg Gly Arg Ser Ala Ala Phe Gly Ile Pro Cys
                165                 170                 175

Thr Asp Lys Phe Val Val Phe Ser Gln Ile Glu Ile Leu Thr Pro Pro
            180                 185                 190

Asn Met Thr Ala Lys Cys Asn Lys Thr His Ser Phe Met His Trp Lys
        195                 200                 205

Met Arg Ser His Phe Asn Arg Lys Phe Arg Tyr Glu Leu Gln Ile Gln
    210                 215                 220

Lys Arg Met Gln Pro Val Ile Thr Glu Gln Val Arg Asp Arg Thr Ser
225                 230                 235                 240

Phe Gln Leu Leu Asn Pro Gly Thr Tyr Thr Val Gln Ile Arg Ala Arg
                245                 250                 255

Glu Arg Val Tyr Glu Phe Leu Ser Ala Trp Ser Thr Pro Gln Arg Phe
            260                 265                 270

Glu Cys Asp Gln Glu Glu Gly Ala Asn Thr Arg Ala Trp Arg Thr Ser
        275                 280                 285

Leu Leu Ile Ala Leu Gly Thr Leu Leu Ala Leu Val Cys Val Phe Val
    290                 295                 300
```

```
Ile Cys Arg Arg Tyr Leu Val Met Gln Arg Leu Phe Pro Arg Ile Pro
305                 310                 315                 320

His Met Lys Asp Pro Ile Gly Asp Ser Phe Gln Asn Asp Lys Leu Val
            325                 330                 335

Val Trp Glu Ala Gly Lys Ala Gly Leu Glu Glu Cys Leu Val Thr Glu
            340                 345                 350

Val Gln Val Val Gln Lys Thr
            355
```

<210> SEQ ID NO 2
<211> LENGTH: 120
<212> TYPE: PRT
<213> ORGANISM: Artificial Sequence
<220> FEATURE:
<223> OTHER INFORMATION: amino acid sequence of a VH of hz7G3

<400> SEQUENCE: 2

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
            35                  40                  45

Gly Asp Ile Ile Pro Ser Asn Gly Ala Thr Phe Tyr Asn Gln Lys Phe
50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
            85                  90                  95

Ala Arg Ser His Leu Leu Arg Ala Ser Trp Phe Ala Tyr Trp Gly Gln
            100                 105                 110

Gly Thr Met Val Thr Val Ser Ser
            115                 120
```

<210> SEQ ID NO 3
<211> LENGTH: 114
<212> TYPE: PRT
<213> ORGANISM: Artificial Sequence
<220> FEATURE:
<223> OTHER INFORMATION: amino acid sequence of a VL of hz7G3

<400> SEQUENCE: 3

```
Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Pro Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
            85                  90                  95

Asp Tyr Ser Tyr Pro Tyr Thr Phe Gly Gln Gly Thr Lys Leu Glu Ile
            100                 105                 110

Lys Arg
```

```
<210> SEQ ID NO 4
<211> LENGTH: 450
<212> TYPE: PRT
<213> ORGANISM: Artificial Sequence
<220> FEATURE:
<223> OTHER INFORMATION: amino acid sequence of a heavy chain of hz7G3

<400> SEQUENCE: 4

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Tyr Met Lys Trp Ala Arg Gln Met Pro Gly Lys Gly Leu Glu Trp Met
            35                  40                  45

Gly Asp Ile Ile Pro Ser Asn Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 5
<211> LENGTH: 220
<212> TYPE: PRT
<213> ORGANISM: Artificial Sequence
<220> FEATURE:
<223> OTHER INFORMATION: amino acid sequence of a light chain of hz7G3

<400> SEQUENCE: 5

Asp Ile Val Met Thr Gln Ser Pro Asp Ser Leu Ala Val Ser Leu Gly
1               5                   10                  15

Glu Arg Ala Thr Ile Asn Cys Glu Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Pro Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Tyr Ser Tyr Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 6
<211> LENGTH: 450
<212> TYPE: PRT
<213> ORGANISM: Artificial Sequence
<220> FEATURE:
<223> OTHER INFORMATION: amino acid sequence of a heavy chain of hz7G3V1

<400> SEQUENCE: 6
```

```
Glu Val Gln Leu Val Gln Ser Gly Ala Glu Val Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
        35                  40                  45

Gly Asp Ile Ile Pro Ser Asn Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Phe Arg
290                 295                 300

Val Val Ser Val Leu Thr Val Val His Gln Asp Trp Leu Asn Gly Lys
305                 310                 315                 320

Glu Tyr Lys Cys Lys Val Ser Asn Lys Ala Leu Pro Ala Pro Glu Glu
            325                 330                 335

Lys Thr Ile Ser Lys Thr Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
            405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 7
<211> LENGTH: 450
<212> TYPE: PRT
<213> ORGANISM: Artificial Sequence
<220> FEATURE:
<223> OTHER INFORMATION: amino acid sequence of a heavy chain of hz7G3V2

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
            20                  25                  30

Tyr Met Lys Trp Ala Arg Gln Met Pro Gly Lys Gly Leu Glu Trp Met
            35                  40                  45

Gly Asp Ile Ile Pro Ser Asn Gly Ala Thr Phe Tyr Asn Gln Lys Phe
    50                  55                  60

Lys Gly Gln Val Thr Ile Ser Ala Asp Lys Ser Ile Ser Thr Thr Tyr
65                  70                  75                  80

Leu Gln Trp Ser Ser Leu Lys Ala Ser Asp Thr Ala Met Tyr Tyr Cys
                85                  90                  95

Ala Arg Ser His Leu Leu Arg Ala Ser Trp Phe Ala Tyr Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Asp Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Phe Arg
    290                 295                 300

Val Val Ser Val Leu Thr Val Val His Gln Asp Trp Leu Asn Gly Lys
305                 310                 315                 320
```

-continued

```
Glu Tyr Lys Cys Lys Val Ser Asn Lys Ala Leu Pro Leu Pro Glu Glu
                325                 330                 335

Lys Thr Ile Ser Lys Thr Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```